United States Patent
Valizadeh et al.

(10) Patent No.: US 11,499,145 B2
(45) Date of Patent: Nov. 15, 2022

(54) TRUNCATED AND MODIFIED SERRATIOPEPTIDASE AND POLYNUCLEOTIDES ENCODING THE SAME

(71) Applicants: Vahideh Valizadeh, Tehran (IR); Maryam Rouhani, Tehran (IR); Dariush Norouzian, Tehran (IR); Reza Ahangari Cohan, Tehran (IR); Sara Mola Salehi, Tehran (IR)

(72) Inventors: Vahideh Valizadeh, Tehran (IR); Maryam Rouhani, Tehran (IR); Dariush Norouzian, Tehran (IR); Reza Ahangari Cohan, Tehran (IR); Sara Mola Salehi, Tehran (IR)

(*) Notice: Subject to any disclaimer, the term of this patent is extended or adjusted under 35 U.S.C. 154(b) by 0 days.

(21) Appl. No.: 17/100,000

(22) Filed: Nov. 17, 2020

(65) Prior Publication Data

US 2021/0062174 A1 Mar. 4, 2021

Related U.S. Application Data

(60) Provisional application No. 62/936,535, filed on Nov. 17, 2019.

(51) Int. Cl.
 *C12N 9/52* (2006.01)

(52) U.S. Cl.
 CPC .......... *C12N 9/52* (2013.01); *C12Y 304/2404* (2013.01)

(58) Field of Classification Search
 CPC .................................................. C12Y 304/2404
 USPC ........................................................ 435/212
 See application file for complete search history.

*Primary Examiner* — Sheridan Swope
(74) *Attorney, Agent, or Firm* — Bajwa IP Law Firm; Haris Zaheer Bajwa

(57) ABSTRACT

A truncated and modified Serratiopeptidase or a variant thereof, and polynucleotides encoding the same. The truncated and modified Serratiopeptidase may have an amino acid sequence including amino acids 1 to 344, and amino acids 1 to 380 of SEQ ID NO: 1. The truncated and modified Serratiopeptidase may further include a first Cysteine (C) residue at a N-terminus of the truncated and modified Serratiopeptidase, substituted for at least one of Alanine 8 and Leucine 12 of SEQ ID NO: 1; and a second Cysteine residue at a C-terminus of the truncated and modified Serratiopeptidase, substituted for at least one of Valine 339 and Arginine 302 of SEQ ID NO: 1. The first and the second Cysteine residues may be adapted to form at least one disulfide bond including at least one of C8-C339, and C12-C302 disulfide bonds between the N-terminus and the C-terminus of the truncated and modified Serratiopeptidase.

1 Claim, 15 Drawing Sheets

Specification includes a Sequence Listing.

TRUNCATED AND MODIFIED SERRATIOPEPTIDASE AND POLYNUCLEOTIDES ENCODING THE SAME

CROSS-REFERENCE TO RELATED APPLICATION

This application claims the benefit of priority from U.S. Provisional Patent Application Ser. No. 62/936,535, filed on Nov. 17, 2019 which is incorporated herein by reference in its entirety.

TECHNICAL FIELD

The present disclosure generally relates to a truncated and modified Serratiopeptidase (also called Serralysin, Serrapeptase, and Serratiapeptidase), polynucleotides encoding the same, methods for production thereof, and compositions comprising the truncated and modified Serratiopeptidase; more particularly, the present disclosure relates to the truncated and modified Serratiopeptidase having about 344 to about 380 amino acid residues.

BACKGROUND

Serratiopeptidase (also known as Serralysin, Serrapeptase, Serratiapeptidase, etc.) is a member of Serralysin family metalloproteases, secreted from a member of Enterobacteriace family *Serratia marcesence*. This enzyme has been widely used for clinical applications including orthopedics, surgery, dentistry and otorhinolaryngology owing to its analgesic, anti-edema, and anti-inflammatory properties. Fibrinolytic and caseinolytic activities of Serratiopeptidase has made it a promising candidate for treating atherosclerosis and cystic fibrosis. Meanwhile, anti-biofilm activity of this metalloprotease prevents bacterial adhesion to abiotic surfaces, in turn, decreasing their invasive power. It's proven that co-administration of Serratiopeptidase with antibiotics such as ampicillin, ciclacillin, cephalexin, minocycline, cefotiam, etc. may improve antibiotic activity by enhancing their dispersion through an infection site.

Despite of the wide range of applications and actions reported for Serratiopeptidase, this enzyme has raised a number of negative issues when employed in different pharmaceutical and industrial applications. Such issues include sensitivity to environmental tensions (such as high temperature and suboptimal pH), low membrane permeability and mucosal penetration, and low bioavailability.

Thereby, production of a stable form of Serratiopeptidase with high functionality, high thermal and pH stability, improved mucosal and membrane permeability, and enhanced anti-biofilm activity is of critical importance to industrial and pharmaceutical applications.

SUMMARY

This summary is intended to provide an overview of the subject matter of the present disclosure, and is not intended to identify essential elements or key elements of the subject matter, nor is it intended to be used to determine the scope of the claimed implementations. Its sole purpose is to present some concepts of one or more aspects in a simplified form as a prelude to the more detailed description that is presented later. The proper scope of the present disclosure may be ascertained from the claims set forth below in view of the detailed description below and the drawings.

In one general aspect, the present disclosure describes a truncated and modified Serratiopeptidase. The truncated and modified Serratiopeptidase may have an amino acid sequence with about 344 to about 380 amino acid residues. In exemplary embodiments, the amino acid sequence may include amino acids 1 to 344, and amino acids 1 to 380 of SEQ ID NO: 1. The truncated and modified Serratiopeptidase may further include a first Cysteine (C) residue at a N-terminus of the truncated and modified Serratiopeptidase that may be substituted for at least one of Alanine 8 and Leucine 12 of SEQ ID NO: 1, and a second Cysteine residue at a C-terminus of the truncated and modified Serratiopeptidase that may be substituted for at least one of Valine 339 and Arginine 302 of SEQ ID NO: 1.

In exemplary embodiments, the first and the second Cysteine residues may be adapted to form at least one disulfide bond between the N-terminus and the C-terminus of the truncated and modified Serratiopeptidase. In an exemplary embodiment, said at least one disulfide bond may include C8-C339, and C12-C302 disulfide bonds.

In one or more exemplary embodiments, the truncated and modified Serratiopeptidase may have an amino acid sequence as set forth in SEQ ID NO: 2 that includes Cysteine 8 and Cysteine 339. The Cysteine 8 and 339 may be adapted to form the C8-C339 disulfide bond between the N-terminus and the C-terminus of the truncated and modified Serratiopeptidase. In exemplary embodiments, the truncated and modified Serratiopeptidase set forth in SEQ ID NO: 2 may have a molecular weight between 37 and 37.5 kDa (kilo Daltons). The truncated and modified Serratiopeptidase as set forth in SEQ ID NO: 2 may have at least 80% residual activity at 90° C. after 10 minutes.

In one or more exemplary embodiments, the truncated and modified Serratiopeptidase may have an amino acid sequence as set forth in SEQ ID NO: 3 that includes Cysteine 8 and Cysteine 339. The Cysteines 8 and 339 may be adapted to form the C8-C339 disulfide bond between the N-terminus and the C-terminus of the truncated and modified Serratiopeptidase. In exemplary embodiments, the truncated and modified Serratiopeptidase set forth in SEQ ID NO: 3 may have a molecular weight between 40.5 and 41 kDa. The truncated and modified Serratiopeptidase with the amino acid sequence set forth in SEQ ID NO: 3 may have at least 70% residual activity at 90° C. after 10 minutes.

In one or more exemplary embodiments, the truncated and modified Serratiopeptidase may have an amino acid sequence as set forth in SEQ ID NO: 4 that includes Cysteine 12 and Cysteine 302. The Cysteine 12 and 302 may be adapted to form the C12-C302 disulfide bond between the N-terminus and the C-terminus of the truncated and modified Serratiopeptidase. In exemplary embodiments, the truncated and modified Serratiopeptidase set forth in SEQ ID NO: 4 may have a molecular weight between 40.2 and 40.8 kDa. The truncated and modified Serratiopeptidase with the amino acid sequence set forth in SEQ ID NO: 4 may have at least 70% residual activity at 90° C. after 10 minutes.

In another aspect, the present disclosure relates to a polynucleotide encoding the truncated and modified Serratiopeptidase. In exemplary embodiments, the polynucleotide may include an open reading frame that encodes one of the amino acid sequences set forth in SEQ ID NOs: 2, 3, and 4. In an exemplary embodiment, the polynucleotide may have a nucleic acid sequence as set forth in SEQ ID NO: 6. The polynucleotide may further include at least one of TGC or TGT at positions 22 to 24, and positions 1015 to 1017 of SEQ ID NO: 6.

In another exemplary embodiment, the polynucleotide may have a nucleic acid sequence as set forth in SEQ ID NO: 7. The polynucleotide may further include at least one of TGC or TGT at positions 22 to 24, and positions 1015 to 1017 of SEQ ID NO: 7.

In another exemplary embodiment, the polynucleotide may have a nucleic acid sequence as set forth in SEQ ID NO: 8. The polynucleotide may further include at least one of TGC or TGT at positions 34 to 36, and positions 904 to 906 of SEQ ID NO: 8. In exemplary embodiments, the at least one of TGC or TGT may encode for Cysteine.

BRIEF DESCRIPTION OF THE DRAWINGS

The novel features which are believed to be characteristic of the present disclosure, as to its structure, organization, use and method of operation, together with further objectives and advantages thereof, will be better understood from the following drawings in which a presently preferred embodiment of the present disclosure will now be illustrated by way of example. It is expressly understood, however, that the drawings are for the purpose of illustration and description only and are not intended as a definition of the limits of the present disclosure. Embodiments of the present disclosure will now be described by way of example in association with the accompanying drawings in which.

DETAILED DESCRIPTION

Figure 1:
FIG. 1 illustrates a schematic three-dimensional structure of a truncated and modified Serratiopeptidase having an amino acid sequence set forth in SEQ ID NO: 2, consistent with one or more embodiments of the present disclosure.

In the following detailed description, numerous specific details are set forth by way of examples to provide a thorough understanding of the relevant teachings related to the exemplary embodiments. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be plain to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

It must be noted that, as used in this specification, the singular forms "a," "an," and "the" include plural referents unless the context clearly dictates otherwise.

As used herein, the terms "comprising," "including," "constituting," "containing," "consisting of," and grammatical equivalents thereof are inclusive or open-ended terms that do not exclude additional, unrecited elements or method steps.

Reference herein to "one embodiment," "an embodiment," "some embodiments," "one or more embodiments," "one exemplary embodiment," "an exemplary embodiment," "some exemplary embodiments," and "one or more exemplary embodiments" indicate that a particular feature, structure or characteristic described in connection or association with the embodiment may be included in at least one of such embodiments. However, the appearance of such phrases in various places in the present disclosure do not necessarily refer to a same embodiment or embodiments.

The word "exemplary" is used herein to mean "serving as an example, instance, or illustration." Any embodiment described herein as "exemplary" is not necessarily to be construed as preferred or advantageous over other embodiments. Likewise, the term "embodiments of the invention" does not require that all embodiments of the invention include the discussed feature, advantage or mode of operation.

The term "about" is used herein to indicate that a value includes the inherent variation of error for the device, the method being employed to determine the value, or the variation that exists among the study subjects.

Provided herein is an exemplary truncated and modified Serratiopeptidase or a variant thereof, polynucleotide(s) encoding the same, and method(s) for producing thereof. The truncated and modified Serratiopeptidase may include one or more modifications that significantly improve the properties of a full-length native Serratiopeptidase. Such improvements may include, but are not limited to, improved thermostability, improved structural stability, increased anti-biofilm activity, improved mucosal penetration and membrane permeability, and increased bioavailability. Exemplary embodiments, consistent with the present disclosure, are described primarily in context of said truncated and modified Serratiopeptidase, amino acid sequence(s) and polynucleotide(s) related thereto, and method(s) of preparation. However, it is apparent to one skilled in the art that other exemplary aspects, embodiments, and implementations pertaining to different applications and products may fall into the context of the exemplary embodiments. Such applications and products may include, but are limited to, any composition/product comprising said exemplary truncated and modified Serratiopeptidase; methods of medical treatments; diagnostic/detection methods, tools, and kits; and any catalytic process related to the exemplary truncated and modified Serratiopeptidase disclosed herein.

The exemplary truncated and modified Serratiopeptidase disclosed herein, and/or the compositions comprising the same may have a wide range of therapeutic effects including, but not limited to, anti-inflammatory effects, analgesic effects, fibrinolytic effects, and anti-bacterial effects (anti-biofilm formation). Thus, the exemplary truncated and modified Serratiopeptidase, and/or the compositions comprising the same may be useful for treating diseases or disorders including, but not limited to, osteoarthritis, rheumatoid arthritis, osteoporosis, fibromyalgia, carpel tunnel syndrome, migraine headache, back pain, tension headache, sinusitis, laryngitis, sore throat, ear infections, swelling after surgery, thrombophlebitis, inflammatory bowel disease (IBD) including ulcerative colitis and Crohn's disease, atherosclerosis, fibrocystic breast disease, breast engorgement, diabetes, leg ulcers, inflammation in prostate gland, asthma, chronic emphysema, and empyema. Meanwhile, the exemplary truncated and modified Serratiopeptidase, and/or the compositions comprising the same may have an improved anti-biofilm activity and may be administered alone or in combination with an antibiotic to treat infectious diseases.

The term "Serratiopeptidase" as used herein refers to a metalloproteinase enzyme produced from a member of Enterobacteriace family, *Seartia marcesence*; and is also known as "Serapeptidase," "Serralysin," "Serratiapeptidase," "Serratiopeptase," etc.

The term "amino acid" as used herein refers to natural and/or unnatural or synthetic amino acids, including both the D and L optical isomers, amino acid variants (for example, norleucine is an analog of leucine) and derivatives known in the art. Generally, in the context of the present application, the peptides and polypeptides are shown in the N- to C-terminal orientation.

The term "polypeptide" as used herein may be implemented interchangeably with the terms "peptide" and "protein", and refers to polymers of at least two amino acids connected by peptide bonds. The polymer may comprise amino acid variants or modified amino acids, it may be linear or branched, and it may be interrupted by non-amino acids. The term also encompasses an amino acid polymer that has been modified naturally or artificially; for example, by disulfide bond formation, glycosylation, lipidation, acetylation, phosphorylation, or any other manipulation, such as conjugation to a labeling moiety. However, in exemplary embodiments, this term relates to polymers of naturally occurring amino acids, as defined below, which may optionally be modified as defined above, but does not comprise non-amino acid moieties in the polymer backbone.

The term "polynucleotide" as used herein may be employed interchangeably with the terms "nucleic acid molecule" or "nucleic acid", and refers to a polymeric form of nucleotides of any length, either deoxyribonucleotides or ribonucleotides, or variants thereof. Nucleic acid molecules may have any three-dimensional structure and may perform any function, known or unknown. The term also encompasses nucleic-acid-like structures with synthetic backbones. A nucleic acid molecule may comprise one or more modified nucleotides, such as methylated nucleotides and nucleotide variants. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

In one general aspect, the present disclosure provides an exemplary truncated and modified Serratiopeptidase or the variant thereof, which may lack at least 120 amino acids from a C-terminus of the full-length native Serratiopeptidase. The full-length native Serratiopeptidase may have an amino acid sequence as set forth in NCBI Accession NO: CAA39139.1, and a three-dimensional structure as illustrated in PDB ID: 5D7W. The full-length native Serratiopeptidase may also include any amino acid sequence with at least 80% sequence identity to that of NCBI Accession NO: CAA39139.1. In exemplary embodiments, said truncated and modified Serratiopeptidase may have an amino acid sequence including amino acids 1 to 344, and amino acids 1 to 380 of SEQ ID NO: 1. The truncated and modified Serratiopeptidase may further include a first Cysteine (C/Cys) residue at a N-terminus of the truncated and modified Serratiopeptidase which may be substituted for at least one of Alanine 8 and Leucine 12 of SEQ ID NO: 1; and a second Cysteine residue at a C-terminus of the truncated and modified Serratiopeptidase that may be substituted for at least one of Valine 339 and Arginine 302. In exemplary embodiments, the first and the second Cysteine residues may be adapted to form at least one disulfide bond between the N-terminus and the C-terminus of the truncated and modified Serratiopeptidase. For example, in an exemplary embodiment, the at least one disulfide bond may be formed by oxidative folding between at least one of Cysteine 8 and Cysteine 339, and/or between Cysteine 12 and Cysteine 302. In exemplary embodiments, the truncated and modified Serratiopeptidase may include at least one disulfide bond selected from the group consisting of C8-C339, C8-C302, C12-C339, C12-C302, and a combination thereof. In an exemplary embodiment, the truncated and modified Serratiopeptidase may have an amino acid sequence as set forth in SEQ ID NO: 2, 3, and/or 4.

The term "variant" as used herein, refers to molecules which differ in their amino acid sequence from a native or reference sequence. The amino acid sequence variants may possess substitutions, deletions, and/or insertions at certain positions within the amino acid sequence, as compared to a native or reference sequence. Ordinarily, variants possess at least 50% identity to a native or reference sequence. In some embodiments, variants share at least 80% or at least 90% identity with a native or reference sequence.

The term "identity" or "identical" as known in the art, refers to a relationship between the sequences of two or more polypeptides or polynucleotides, as determined by comparing the sequences. In the art, identity also means the degree of sequence relatedness between them as determined by the number of matches between strings of two or more amino acid residues or nucleic acid residues. Identity measures the percent of identical matches between the smaller of two or more sequences with gap alignments (if any) addressed by a particular mathematical model or computer program (e.g. "algorithms"). Identity of related peptides may be readily calculated by known methods. "% identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. It is understood that identity depends on a calculation of percent identity but may differ in value due to gaps and penalties introduced in the calculation. Generally, variants of a particular polynucleotide or polypeptide have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. In exemplary embodiments, the length of a sequence aligned for comparison purposes may be at least 30%, at least 40%, at least 50%, at least 60%, at least 70%, at least 80%, at least 90%, at least 95%, or 100% of the length of the reference sequence. The nucleotides at corresponding nucleotide positions may then be compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences.

As used herein, the terms "termini" or "terminus" when referring to polypeptides or polynucleotides refers to an extremity of a polypeptide or polynucleotide respectively. Such extremity is not limited only to the first or final site of the polypeptide or polynucleotide but may include additional amino acids or nucleotides in the terminal regions. Polypeptide-based molecules may be characterized as having both an N-terminus (terminated by an amino acid with a free amino group (NH2)) and a C-terminus (terminated by an amino acid with a free carboxyl group (COOH)). Proteins are in some cases made up of multiple polypeptide chains brought together by disulfide bonds or by non-covalent forces (multimers, oligomers). These proteins have multiple N- and C-termini. Alternatively, the termini of the polypeptides may be modified such that they begin or end, as the case may be, with a non-polypeptide based moiety such as an organic conjugate.

In other exemplary embodiments, the truncated and modified Serratiopeptidase may include an amino acid sequence with at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% sequence identity to SEQ ID NOs: 2, 3, and/or 4. In an exemplary embodiment, said amino acid sequence may be at least 95 to 99.5% identical to SEQ ID NOs: 2, 3, and/or 4. In an exemplary embodiment, said amino acid sequence may be at least 98% identical to SEQ ID NO: 2.

In exemplary embodiments, the truncated and modified Serratiopeptidase may include an amino acid sequence with at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% sequence homology to SEQ ID NOs: 2, 3, and/or 4. In an exemplary embodiment, said amino acid sequence may be at least 95 to 99.5% homologous to SEQ ID NOs: 2, 3, and/or 4. In an exemplary embodiment, said amino acid sequence may be at least 98% homologous to SEQ ID NO: 2.

The term "homology" as used herein implies that the compared sequences diverged in evolution from a common origin. The term "homolog" refers to a first amino acid sequence or nucleic acid sequence (e.g., gene (DNA or RNA) or protein sequence) that is related to a second amino acid sequence or nucleic acid sequence by descent from a common ancestral sequence. The term "homolog" may apply to the relationship between genes and/or proteins separated by the event of speciation or to the relationship between genes and/or proteins separated by the event of genetic duplication. "Orthologs" are genes (or proteins) in different species that evolved from a common ancestral gene (or protein) by speciation. Typically, orthologs retain the same function in the course of evolution. "Paralogs" are genes (or proteins) related by duplication within a genome. Orthologs retain the same function in the course of evolution, whereas paralogs evolve new functions, even if these are related to the original one.

The term "homologous" as used herein refer to a comparison between at least two sequences (polynucleotide or polypeptide sequences). Two polynucleotide sequences are considered homologous if the polypeptides they encode are at least 50%, 60%, 70%, 80%, 90%, 95%, or even 99% for at least one stretch of at least 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. Two protein sequences may be considered homologous if the proteins are at least 50%, 60%, 70%, 80%, or 90% identical for at least one stretch of at least 20 amino acids.

Figure 2:
FIG. 2 illustrates a schematic three-dimensional structure of a truncated and modified Serratiopeptidase having an amino acid sequence set forth in SEQ ID NO: 3, consistent with one or more embodiments of the present disclosure.
Figure 3:
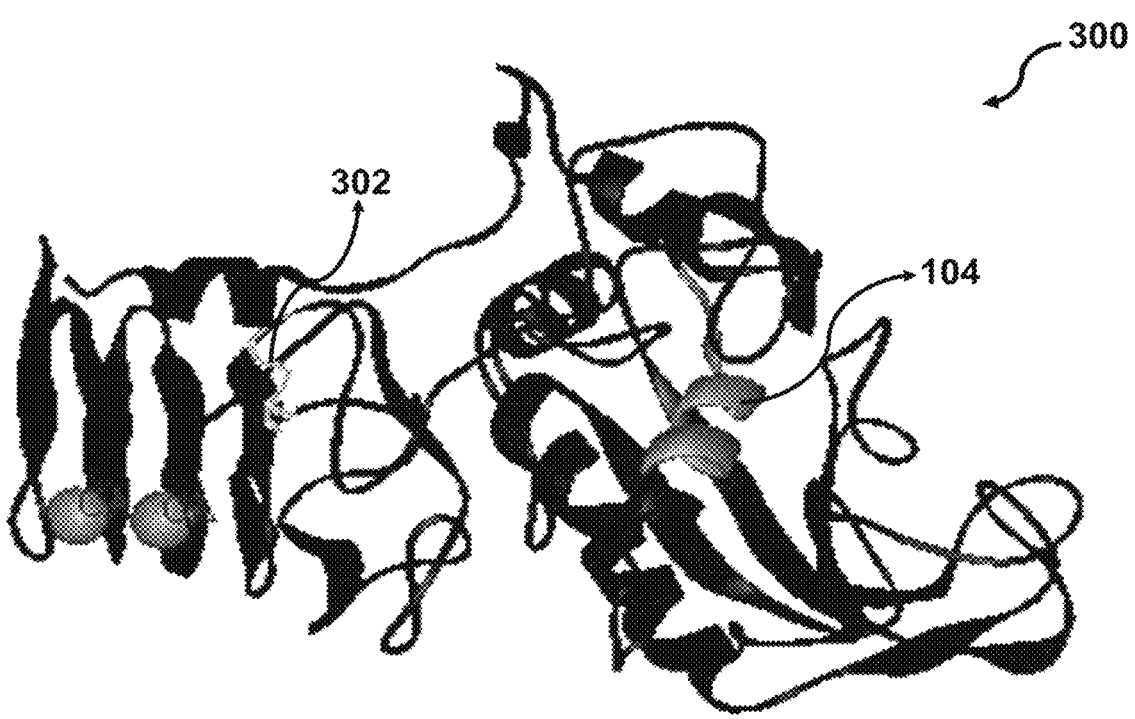
FIG. 3 illustrates a schematic three-dimensional structure of a truncated and modified Serratiopeptidase having an amino acid sequence set forth in SEQ ID NO: 4, consistent with one or more embodiments of the present disclosure.

Referring to the drawings, FIGS. 1-3 illustrate exemplary embodiments of the truncated and modified Serratiopeptidase, consistent with the present disclosure. FIG. 1 shows a schematic three-dimensional structure of the truncated and modified Serratiopeptidase 100 having the amino acid sequence set forth in SEQ ID NO: 2, consistent with one or more embodiments of the present disclosure. In an exemplary embodiment, the truncated and modified Serratiopeptidase 100 comprises 344 amino acids and may include the first Cysteine residue at position 8 (C8) and the second Cysteine residue at position 339 (C339). The C8 and C339 may be adapted to form the C8-C339 disulfide bond 102 between the N-terminus and the C-terminus of the truncated and modified Serratiopeptidase 100. Similar to the full-length native Serratiopeptidase, the truncated and modified Serratiopeptidase 100 may further include a catalytic domain 104 and a plurality of calcium and zinc ions. The truncated and modified Serratiopeptidase 100 may have a molecular weight between 36 and 38 KiloDaltons (kDa), in particular between 37 and 37.5 kDa. In an exemplary embodiment, the truncated and modified Serratiopeptidase 100 may have a molecular weight of 37.21 kDa. In an exemplary embodiment, the truncated and modified Serratiopeptidase 100 may have at least 80% residual activity at 90° C. after 10 minutes. As used herein, the term "residual activity" refers to ratio of activity with respect to a substrate measured with and without incubation at a specific condition (such as, without limitation, altered temperature or altered pH).

FIG. 2 illustrates a schematic three-dimensional structure of the truncated and modified Serratiopeptidase 200 having the amino acid sequence set forth in SEQ ID NO: 3, consistent with one or more embodiments of the present disclosure. In an exemplary embodiment, the truncated and modified Serratiopeptidase 200 comprises 380 amino acids and may include the first Cysteine residue at position 8 (C8) and the second Cysteine residue at position 339 (C339). The C8 and C339 may be adapted to form the C8-C339 disulfide bond 102 between the N-terminus and the C-terminus of the truncated and modified Serratiopeptidase 200. Similar to the full-length native Serratiopeptidase, the truncated and modified Serratiopeptidase 200 may further include the catalytic domain 104 and the plurality of calcium and zinc ions. The truncated and modified Serratiopeptidase 200 may have a molecular weight between 39 and 41 kDa, in particular between 40.5 and 41 kDa. In an exemplary embodiment, the truncated and modified Serratiopeptidase 200 may have a molecular weight of 40.67 kDa. The truncated and modified Serratiopeptidase with the amino acid sequence set forth in SEQ ID NO: 3 may have at least 70% residual activity at 90° C. after 10 minutes. In an exemplary embodiment, the truncated and modified Serratiopeptidase 200 may have at least 70% residual activity at 90° C. after 10 minutes.

FIG. 3 shows a schematic three-dimensional structure of the truncated and modified Serratiopeptidase 300 having the amino acid sequence set forth in SEQ ID NO: 4, consistent with one or more embodiments of the present disclosure. In an exemplary embodiment, the truncated and modified Serratiopeptidase 300 comprises 380 amino acids and may include the first Cysteine residue at position 12 (C12) and the second Cysteine residue at position 302 (C302). The C12 and C302 may be configured to form the C12-C302 disulfide bond 302 between the N-terminus and the C-terminus of the truncated and modified Serratiopeptidase 300. Similar to the full-length native Serratiopeptidase, the truncated and modified Serratiopeptidase 300 may further include a catalytic domain 104 and the plurality of calcium and zinc ions. The truncated and modified Serratiopeptidase 100 may have a molecular weight between 39 and 41 KiloDaltons (kDa), in particular between 40.2 and 40.8 kDa. In an exemplary embodiment, the truncated and modified Serratiopeptidase 100 may have a molecular weight of 40.57 kDa. In an exemplary embodiment, the truncated and modified Serratiopeptidase 300 with the amino acid sequence set forth in SEQ ID NO: 3 may have at least 70% residual activity at 90° C. after 10 minutes.

Another aspect of the present disclosure directs to an exemplary polynucleotide/nucleic acid molecule encoding the truncated and modified Serratiopeptidase (100, 200, and/or 300) or the variant thereof. In particular, said polynucleotide/nucleic acid molecule may include an open reading frame that encodes the truncated and modified Serratiopeptidase (100, 200, and/or 300) or the variant thereof. The polynucleotide/nucleic acid molecule may include RNA, and single- or double-stranded DNA. In exemplary embodiments, the polynucleotide and/or the open reading frame may lack at least 370 base-pairs (bp) from a 3'-end of a full-length native Serratiopeptidase gene; and may have a nucleic acid sequence including nucleotides 1 to 1032 of SEQ ID NO: 5, and/or nucleotides 1 to 1140 of SEQ ID NO: 5. In exemplary embodiments, the polynucleotide and/or the open reading frame may further include a first plurality of mutations at 5'-end and a second plurality of mutations at 3'-end. The first plurality of mutations may include, but is not limited to, at least one of nucleotides 22 to 24 of SEQ ID NO: 5 adapted to substitute at least one of TGC or TGT for GCG, and nucleotides 34 to 36 of SEQ ID NO: 5 adapted to substitute at least one of TGC or TGT for CGT. The second plurality of mutations may include, but is not limited to, nucleotides 904 to 906 of SEQ ID NO: 5 adapted to substitute at least one of TGC or TGT for CTG, and nucleotides 1015 to 1017 of SEQ ID NO: 5 adapted to substitute at least one of TGC or TGT for GTG. In an exemplary embodiment, the polynucleotide and/or the open reading frame may include a nucleic acid sequence as set forth in SEQ ID NOs: 6, 7, and/or 8.

In exemplary embodiments, the at least one of TGC or TGT may encode for Cysteine residue. For example, the TGC at positions corresponding to nucleotides 22 to 24 and nucleotides 1015 to 1017 of SEQ ID NOs: 6 and 7 may encode for Cysteine 8 and Cysteine 339, respectively. On the other hand, the TGC at positions corresponding to nucleotides 34 to 36 and nucleotides 904 to 906 of SEQ ID NO: 8 may encode for Cysteine 12 and Cysteine 302, respectively.

The term "open reading frame" or "ORF" as used herein, refers to a series of nucleotide triplets coding for amino acids without any termination codons and is a sequence translatable into protein.

In other exemplary embodiments, the polynucleotide and/or the open reading frame may include a nucleic acid sequence with at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% sequence identity to SEQ ID NOs: 6, 7, and/or 8. In an exemplary embodiment, said nucleotide sequence may be at least 95 to 99.5% identical to SEQ ID NO: 6, 7, and/or 8. In an exemplary embodiment, said nucleic acid sequence may be at least 98% identical to SEQ ID NO: 6.

It is to be understood that the various polypeptides and polynucleotides having at least one of aforementioned mutations, even if their amino acid sequences are not explicitly described herein for the sake of conciseness, are contemplated to be within the scope of the exemplary embodiments. As such, polynucleotides encoding peptides or polypeptides containing substitutions, insertions and/or additions, deletions and covalent modifications with respect to reference sequences, in particular the polypeptide sequences disclosed herein, are included within the scope of this disclosure. For example, sequence tags or amino acids, such as one or more Lysines, may be added to peptide sequences (e.g. at the N-terminal or C-terminal ends).

In some exemplary embodiments, said polynucleotide may comprise a modification or sequence that provides for an additional desirable feature (e.g., modified or regulated stability; subcellular targeting; tracking, e.g., a fluorescent label; a binding site for a protein or protein complex; etc.). Non-limiting examples include: a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin)); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, etc.); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); and combinations thereof.

Figure 4:
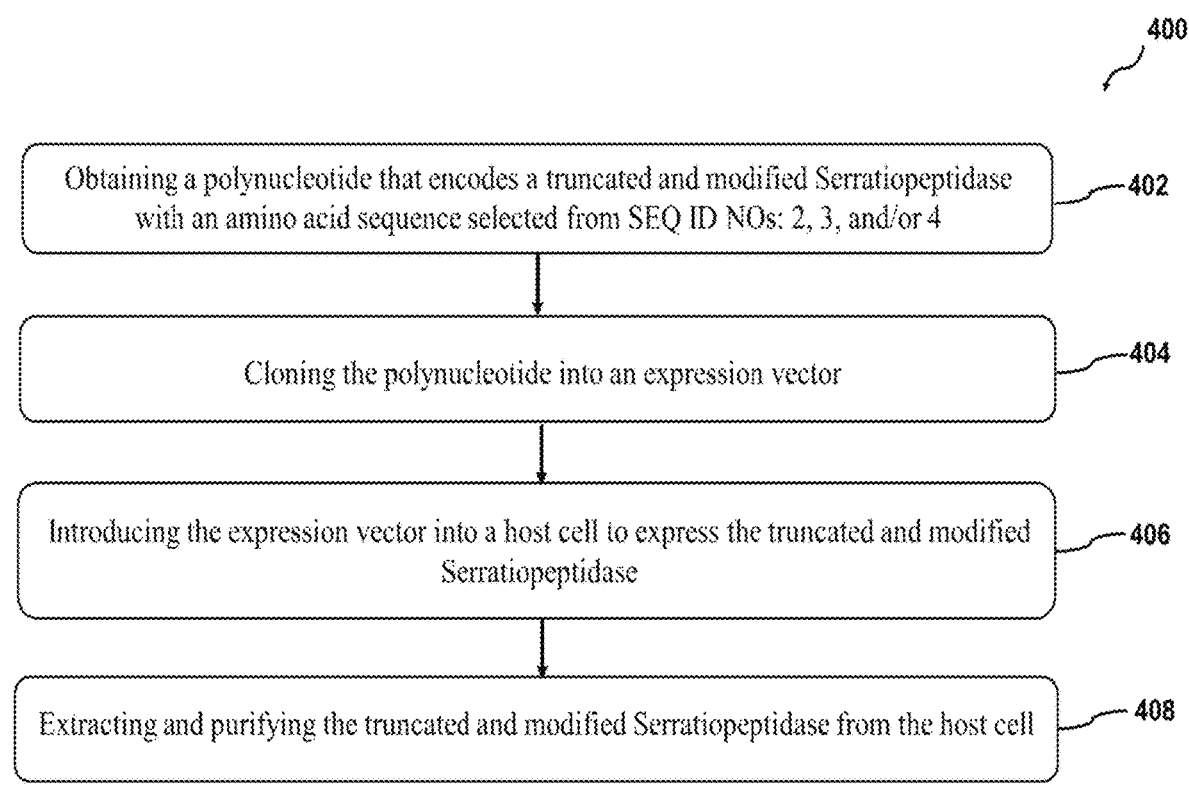
FIG. 4 illustrates a process flow diagram illustrating an exemplary method for producing the truncated and modified Serratiopeptidase (SEQ ID NOs: 2, 3, and 4), consistent with exemplary embodiments of the present disclosure.

Other aspects of the present disclosure provide an exemplary method for producing said truncated and modified Serratiopeptidase (100, 200, and/or 300) or the variant thereof. FIG. 4 illustrates a process flow diagram illustrating the exemplary method 400 for producing the truncated and modified Serratiopeptidase (100, 200, and 300), consistent with exemplary embodiments of the present disclosure. The exemplary method 400 may include one or more steps with regards to the aspects and embodiments described above, however is not limited thereto.

Step 402 may include obtaining the polynucleotide that encodes the truncated and modified Serratiopeptidase (100, 200, and 300) with amino acid sequences set forth in SEQ ID NOs: 2, 3 and/or 4, respectively. The polynucleotide may have the nucleic acid sequence selected from SEQ ID NOs: 6, 7, and/or 8. In an exemplary embodiment, the polynucleotide may be amplified using the nucleic acid sequence of SEQ ID NO: 5 as template, and at least one pair of specific primers that are capable of introducing at least one of TGC or TGT into said polynucleotide. For example, in order to obtain the nucleic acid sequence of SEQ ID NO: 6, a forward primer set forth in SEQ ID NO: 9 and a reverse primer set forth in SEQ ID NO: 10 may be used. The nucleic acid sequences set forth in SEQ ID NOs: 7 and 8 may be obtained by performing an overlap-polymerase chain reaction (PCR) that includes a first and a second PCR. The first PCR may be adapted to amplify a first and a second fragment of SEQ ID NOs: 7 and 8, and the second PCR may be adapted to amplify an entire sequence length of SEQ ID NOs: 7 and 8. In an exemplary embodiment, primers set forth in SEQ ID NOs: 11 through 16 may be used to amplify the entire sequence of SEQ ID NO: 7, and primers set forth in SEQ ID NOs: 17 through 22 may be used to amplify the entire sequence of SEQ ID NO: 8. In other exemplary embodiments, the polynucleotide may be prepared synthetically, preferably using a commercially available oligo/gene synthesizers.

The terms "overlap-PCR" as used herein refers to a PCR-based method of producing chimeric genes by recombining DNA molecules at a precise junction irrespective of nucleotide sequence at the recombination site. In its simplest form, the two DNA molecules that need to be recombined are amplified in two separate PCR reactions using two separate primer pairs. The 5' ends of the reverse primer for the first DNA molecule and the forward primer for the second DNA molecule have overhangs complementary to each other. This makes the products of these first reactions overlap, that is, they share complementary sequences at the ends to be joined.

Step 404 may include molecular cloning of the polynucleotide having one of the nucleic acid sequences set forth in SEQ ID NOs: 6, 7, and/or 8 into an expression vector. In an exemplary embodiment, Molecular cloning may be used to construct recombinant DNA and may involve the amplification of a DNA fragment of interest and then inserting the fragment into a cloning vector. The recombinant DNA may then be transferred into a host cell/organism which may then be screened and selected for the presence of the inserted recombinant DNA.

As used herein, a "vector" may refer to a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with proper control elements. In general, the term "vector" refers to a nucleic acid molecule capable of transporting another nucleic acid to which it has been linked. Vectors may include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which may refer to a circular double stranded DNA loop into which additional DNA segments may be inserted, such as by standard molecular cloning techniques. Another type of vector may be a viral vector, wherein virally-derived DNA or RNA sequences are present in the vector for packaging into a virus (e.g. retroviruses, replication defective retroviruses, adenoviruses, replication defective adenoviruses, and adeno-associated viruses). Viral vectors may also include polynucleotides carried by a virus for transfection into a host cell. Certain vectors may be capable of autonomous replication in a host cell into which they are introduced (e.g. bacterial vectors having a bacterial origin of replication and episomal mammalian vectors). Other vectors (e.g., non-episomal mammalian vectors) may be integrated into the genome of a host cell upon introduction into the host cell, and thereby may be replicated along with the host genome. Moreover, certain vectors may direct the expression of genes to which they are operatively-linked. Such vectors may be referred to herein as "expression vectors". Common expression vectors of utility in recombinant DNA techniques are often in the form of plasmids. Further discussion of vectors is provided herein. Recombinant expression vectors may comprise a polynucleotide/nucleic acid molecule of the exemplary embodiments in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). In various embodiments, the vector may further comprises regulatory elements for controlling expression of the polypeptide.

In exemplary embodiments, the choice of vector may depend on the host cell/organism into which it is to be transformed. Thus, the vector may be an autonomously replicating vector, i.e. a vector which may exist as an extra-chromosomal entity, the replication of which may be independent of chromosomal replication, e.g. a plasmid. Alternatively, the vector may be one which, when transformed into a host cell/organism, may be integrated into the host cell/organism genome, in part or in its entirety, and replicated together with the chromosomes into which it has been integrated.

As used herein, the terms "transformation", "transformed", "transforming" and the like refer to transfer of a nucleic acid fragment into a host organism/cell either in the form of plasmid or integrated stably to the chromosome of the host organisms resulting in genetically stable inheritance.

The term "host cell/organism" refers to a cell which has been transformed, or is capable of transformation, by an exogenous DNA sequence. The host cell/organism may include, but is not limited to prokaryotic cells such as *E. coli* cells, and eukaryotic cells such as yeast cells, insect cells, plant cells and animal cells (such as mammalian cells, for example, mouse cells, human cells, etc.).

In exemplary embodiments, the expression vector may comprise at least one origin of replication (Ori), a drug-resistance marker (such as an antibiotic-resistance marker), a promoter adapted to provide a binding site for transcription initiation of a gene of interest (i.e. the truncated and modified Serratiopeptidase 100, 200, or 300), one or more regulatory elements, a ribosomal binding site (RBS), a transcription termination site, a Poly-A (polyadenylation) Tail (adapted for protecting mRNA from degradation by nucleases, and terminating transcription and translation procedures), a reporter gene (adapted to produce a reporter protein which may be detected and quantified with a simple assay), and a polylinker/multiple cloning site having a plurality of restriction sites. In exemplary embodiments, the promoter may include, but is not limited to, lac, trp, tac, λPL, GAP (glucose aldehyde 3-phosphate), AOX1, GAL1, GAL10, nmt1, nmt42, and nmt81 promoters. The antibiotic-resistance marker may be adapted to provide antibiotic-resistance for vector-containing bacteria, and to allow their easy detection on a selective media (an antibiotic-supplemented growth media). In exemplary embodiments, the reporter gene may be used to measure efficiency of gene expression and also to detect intracellular localization of the expressed protein (i.e. the truncated and modified Serratiopeptidase 100, 200, or 300). The reporter gene may include lac Z gene, CAT (chloramphenicol acetyltransferase) gene, Luciferase encoding gene, and Luciferase encoding gene, etc. In exemplary embodiments, the one or more regulatory elements may include, but are not limited to, enhancers and promoters. In exemplary embodiments, sequence tags may be used for detection, purification or localization of the truncated and modified Serratiopeptidase (100, 200, or 300). The term "multiple cloning site (MCS)" or "cloning site" or "polylinker" refers to a segment on a vector, which may be suitable for insertion of a nucleic acid sequence, e.g., a nucleic acid sequence comprising an open reading frame (e.g. the polynucleotide(s) encoding the truncated and modified Serratiopeptidase). Insertion may be performed by any molecular biological method known to the one skilled in the art, e.g. by restriction and ligation. A cloning site typically comprises one or more restriction enzyme recognition sites (restriction sites). These one or more restrictions sites may be recognized by restriction enzymes which cleave the DNA at these sites.

Figure 14:
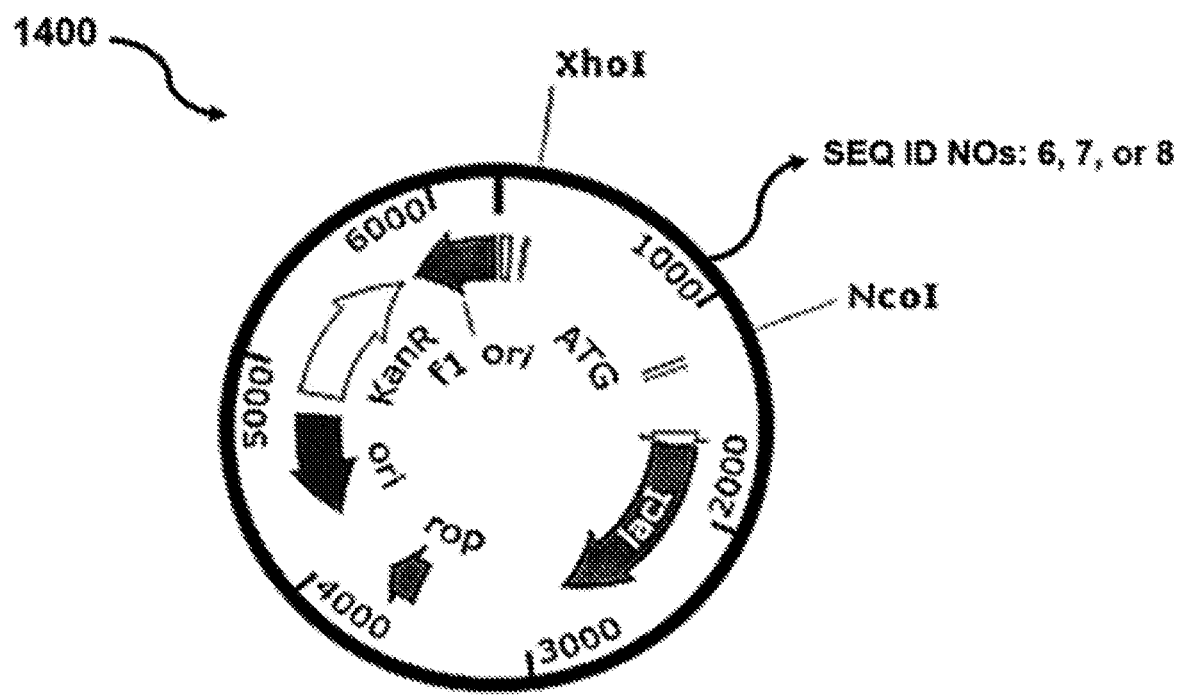
FIG. 14 shows an exemplary expression vector (pET 28a) harboring the nucleic acid sequence set forth in SEQ ID NOs: 6, 7 or 8, consistent with one or more embodiments of the present disclosure.

FIG. 14 shows an exemplary expression vector (pET 28a) 1400 harboring the nucleic acid sequence set forth in SEQ ID NOs: 6, 7 or 8, consistent with one or more embodiments of the present disclosure. In an exemplary embodiment, the expression vector (pET 28a) 1400 may include a repressor of primer (Rop) adapted to control vector copy number.

The term "origin of replication (ori)" or "replication origin" as used herein refers to a region on a vector where DNA replication begins, enabling the vector to reproduce itself as it must to survive within cells.

The term "ribosomal binding site (RB S)" as used herein refers to a region on a vector which may be disposed downstream of the promoter, and may be responsible for efficient translation of the cloned gene.

The term "transcription termination site" or "terminator" refers to DNA sequences located downstream of a coding sequence that ends protein synthesis.

The term "enhancer" refers to a DNA sequence that may stimulate promoter activity and may be an innate element of the promoter or a heterologous element inserted to enhance the transcription level or specificity of a promoter.

The term "expressed protein" or "protein expression" refers to production of a protein within a host cell such as a bacteria, yeast, plant, or animal cell.

Step 406 may include transforming the expression vector into a host cell to express the truncated and modified Serratiopeptidase (100, 200, and/or 300). For example, in an exemplary embodiment, the host cell/organism may be an *Escherichia coli* (*E. coli*) strain. Said *E. coli* strain may include, but is not limited to: GI698, ER2566, BL21 (DE3), B834 (DE3), BLR (DE3), M15 and the like, which are known in the art and are available on the market.

In exemplary embodiments, transforming the expression vector into the host cell/organism may include any method by which nucleic acids may be transferred into the host cell/organism, and may be performed using a suitable standard technique selected according to the kind of host cell/organism. Such methods may include, but are not limited to, electroporation, protoplast fusion, calcium phosphate ($CaPO_4$) precipitation, calcium chloride ($CaCl_2$) precipitation, agitation with silicon carbide fiber, and agrobacterium-, PEG-, dextran sulfate-, lipofectamine- and desiccation/inhibition-mediated transformation, etc.

Step 408, may include extracting and purifying the truncated and modified Serratiopeptidase (100, 200, and/or 300) from the host cell/organism using an extraction and purification method. In particular, extraction of the truncated and modified Serratiopeptidase (100, 200, and/or 300), may be accomplished by disrupting the host cells/organism using various methods including, but not limited to, homogenizer disrupting, ultrasonic treatment, grinding, high pressure extrusion, lysozyme treatment, etc. The purification methods as stated in the step 408 may include, but are not limited to, precipitation and differential solubilization, ultracentrifugation, gradient centrifugation, and chromatography. Furthermore, the step 408 may further include removing reductant from the truncated and modified Serratiopeptidase (100, 200, and/or 300) using exemplary methods including, but not limited to, dialysis, ultrafiltration, and chromatography.

It is to be understood that the amino acid sequences disclosed herein may be prepared recombinantly or by in vitro transcription/translation. The amino acid sequences may also be prepared synthetically, preferably using a commercially available peptide synthesizer. Methods of synthetic peptide synthesis include, but are not limited to liquid-phase peptide synthesis, solid-phase peptide synthesis, and other techniques known in the art.

In another aspect, the present disclosure further relates to an exemplary composition comprising the truncated and modified Serratiopeptidase (100, 200, and/or 300) or the variant thereof, the polynucleotide(s), or the vector(s), and/or the host cell.

Another aspect of the present disclosure relates to an exemplary pharmaceutical composition comprising the truncated and modified Serratiopeptidase (100, 200, and/or 300) or the variant thereof, and optionally, a pharmaceutically acceptable carrier and/or excipient. The pharmaceutical composition consistent with exemplary embodiments may be useful for preventing or treating inflammation and pain, blood clot formation, and bacterial infection. The pharmaceutical composition according to the exemplary embodiments may be useful for treating diseases or disorders including, but not limited to, osteoarthritis, rheumatoid arthritis, osteoporosis, fibromyalgia, carpel tunnel syndrome, migraine headache, back pain, tension headache, sinusitis, laryngitis, sore throat, ear infections, swelling after surgery, thrombophlebitis, inflammatory bowel disease (IBD) including ulcerative colitis and Crohn's disease, atherosclerosis, fibrocystic breast disease, breast engorgement, diabetes, leg ulcers, inflammation in prostate gland, asthma, chronic emphysema, and empyema. Furthermore, the pharmaceutical composition according to the exemplary embodiments may be useful for treating infectious diseases caused by bacteria, such as *Staphylococcus aureus*.

The term "treating" or "treatment" or "therapy" refers to partially or completely alleviating, ameliorating, improving, relieving, delaying onset of, inhibiting progression of, reducing severity of, and/or reducing incidence of one or more symptoms or features of a disease, e.g., a PFIC. For example, "treating" a PFIC may refer to diminishing symptoms associate with the disease, prolong the lifespan (increase the survival rate) of patients, reducing the severity of the disease, preventing or delaying the onset of the disease, etc. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

As discussed, an exemplary pharmaceutical composition may further comprise a pharmaceutically acceptable carrier, excipient, stabilizer or an additional agent capable of providing advantageous properties for administration of the pharmaceutical composition (e.g., administration to a human subject). Suitable pharmaceutical carriers may include, but are not limited to, sterile water, saline, glucose, condensation product of castor oil and ethylene oxide, liquid acid, lower alcohol (e.g., $C_{1-4}$ alcohol), oil (e.g., corn oil, peanut oil, sesame oil; optionally, further comprising an emulsifier such as fatty acid monoglyceride or diglyceride, or phospholipid such as lecithin), ethylene glycol, polyalkylene glycol, sodium alginate, polyvinyl pyrrolidone, and the like. Optionally, exemplary carriers may further include an adjuvant, a preservative, a stabilizer, a moistening agent, an emulsifier, a penetration enhancer, and the like. In some exemplary embodiments, an exemplary pharmaceutical composition may be sterile. In addition, the viscosity of an exemplary pharmaceutical composition may be controlled and maintained by selecting a suitable solvent or excipient.

The term "a pharmaceutically acceptable carrier and/or excipient" refers to a carrier and/or excipient that is pharmacologically and/or physiologically compatible to a subject and active ingredients, which is well known in the art, and includes, but is not limited to: pH regulators, surfactants, and ionic strength enhancers. For example, pH regulators may include, but are not limited to, phosphate buffers; surfactants including, but not limited to: cation surfactants, anion surfactants, or non-ionic surfactants such as Tween-80; and ionic strength enhancers include, but are not limited to, NaCl.

An exemplary pharmaceutical composition may be administered by means well known in the art, for example, including, but not limited to oral administration or injection. In some exemplary embodiments, the pharmaceutical composition may be administered in form of a unit dose. The amount of an exemplary pharmaceutical composition necessary for preventing or treating a specific condition depends on the administration route, the severity of the condition to be treated, the gender, age, body weight and general healthy condition of a patient, and the like, and may be reasonably determined by a physician according to practical conditions.

Other aspects of exemplary embodiments may be directed to antibodies raised against the truncated and modified Serratiopeptidase (100, 200, and/or 300) or the variant thereof, and/or to fragment(s) thereof. Said antibodies may include polyclonal antibodies and monoclonal antibodies which are specific for the truncated and modified Serratiopeptidase (100, 200, and/or 300) or the variant thereof. It would be apparent to one skilled in the art that, in some exemplary embodiments, fragments of such antibodies may also be used for binding to the truncated and modified Serratiopeptidase (100, 200, and/or 300) or the variant thereof. Such antibodies or fragments thereof may be used to detect the presence of the truncated and modified Serratiopeptidase (100, 200, and/or 300) or the variant thereof in a sample (or to detect the presence of a fragment of the truncated and modified Serratiopeptidase (100, 200, and/or 300) or the variant thereof), by putting the sample in contact with the antibody or the fragment thereof. The antibody or the fragment thereof may bind to the truncated and modified Serratiopeptidase (100, 200, and/or 300) or the variant thereof, or the fragment thereof present in the sample, forming a complex therewith.

The polypeptides and nucleic acid molecules described above may preferably be non-naturally occurring. Exemplary embodiments may provide the polypeptides and nucleic acid molecules preferably in recombinant, synthetic, isolated, and/or purified form.

The term "synthetic" means produced, prepared, and/or manufactured by the hand of man. Synthesis of polynucleotides or other molecules of the exemplary embodiments may be chemical or enzymatic.

EXAMPLES

Hereinafter, the present disclosure will be described in further detail with reference to examples. It will be obvious to a person having ordinary skill in the art that these examples are illustrative purposes only and are not to be construed to limit the scope of the present disclosure.

Example 1: Selection of an Appropriate Template for Producing the Truncated and Modified Serratiopeptidase Four crystal structures of Serratiopeptidase derived from Serratia species have been deposited in protein data bank (PDB) entitled "1sat", "1smp", "1srp", and "5D7W" with a resolution of 1.8, 2.3, 2.0, and 1.1 Å, respectively. Structurally, the catalytic domain of Serratiopeptidase comprises a large N-terminus lobe with five-stranded sheets, three helices, and a small C-terminus lobe assembled from a helix and an irregular structure. The $Zn_{2+}$ binding pocket is located in a groove between the lobes. The crystal structure of Serratiopeptidase (PDB ID: 5D7W) has been determined based on the Serratiopeptidase secreted from the bacterial strain Serratia sp. FS14. According to Wu et al. (2016), the 5D7W Serratiopeptidase may retain 40% of its protease activity after incubation at 363 K for 10 min. Since, resistance to environmental tensions like extreme temperatures is of critical importance in development of enzymes, 5D7W may be used as initial template for producing the truncated and modified Serratiopeptidase (100, 200, and 300). Furthermore, 5D7W has the highest resolution (1.1 Å) amongst the four available templates; therefore, it may be a promising candidate for obtaining a high quality and more stable enzyme.

Example 2: Production of the Polynucleotide(s) Encoding the Truncated and Modified Serratiopeptidase The gene encoding full-length Serratiopeptidase (5D7W) was extracted from NCBI and synthesized using a solid-phase oligonucleotide synthesis method after codon optimization (the codon-optimized nucleic acid sequence used as template is set forth in SEQ ID NO: 1). The nucleic acid sequence set forth in SEQ ID NO: 6 was obtained by PCR-amplification of the nucleic acid sequence of SEQ ID NO: 1 using specific forward primer (SE1 ID NO: 9) and reverse primer (SEQ ID NO: 10). On the other hand, the nucleic acid sequences set forth in SEQ ID NOs: 7 and 8 were obtained by overlap PCR. The overlap PCR includes the first PCR for amplifying the first and the second fragments of SEQ ID NOs: 7 and 8, and the second PCR that amplifies entire sequence of SEQ ID NOs: 7 and 8.

Figure 5:
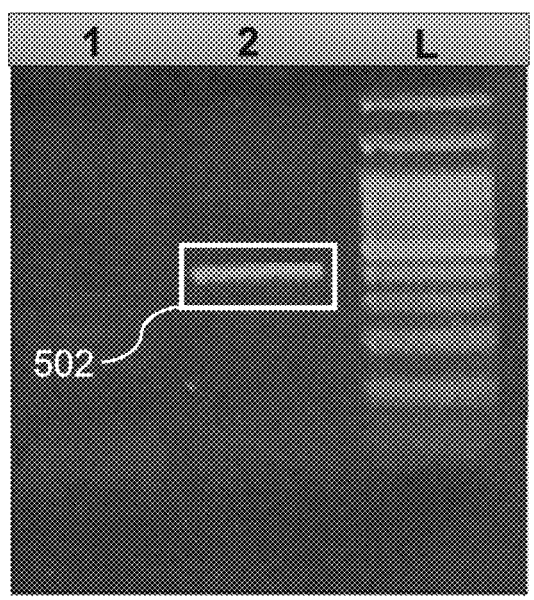
FIG. 5 shows agarose gel electrophoresis profile of PCR (polymerase chain reaction)-amplified polynucleotide set forth in SEQ ID NO: 6 using specific primers (SEQ ID NOs: 9, and 10), consistent with one or more exemplary embodiments of the present disclosure.

PCR products were electrophoresed on 1% agarose gel and the band of engineered protein was observed in the desired range. FIG. 5 shows agarose gel electrophoresis profile of PCR-amplified polynucleotide set forth in SEQ ID NO: 6 (Lane 2) using specific primers (SEQ ID NOs: 9, and 10), consistent with one or more exemplary embodiments of the present disclosure. As shown in FIG. 5, Lane 1 is a negative control devoid of template DNA (i.e., the polynucleotide as set forth in SEQ ID NO: 6); and Lane L is a 1 Kb DNA ladder/marker. In consistence with exemplary embodiments, the agarose gel electrophoresis revealed a 1032 bp DNA band 502 in Lane 2.

Figure 6A:
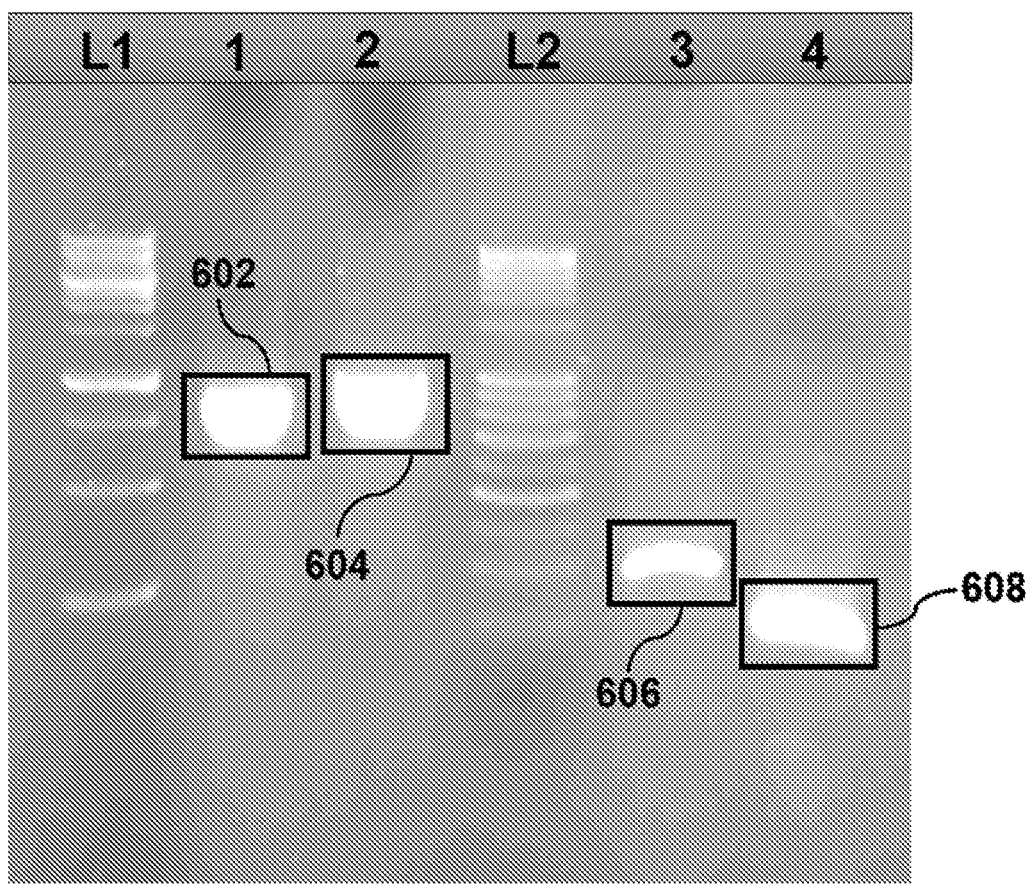
FIG. 6A shows agarose gel electrophoresis results of first PCR of an overlap PCR for obtaining a first and a second fragment of SEQ ID NOs: 7 and 8, consistent with one or more exemplary embodiments of the present disclosure.

FIG. 6A illustrates agarose gel electrophoresis results of the first PCR of an overlap-PCR for obtaining the first and the second fragment of SEQ ID NOs: 7 and 8, consistent with one or more exemplary embodiments of the present disclosure. Lane L1 is a 1 Kb DNA ladder/marker; Lane 1 is the first fragment of SEQ ID NO: 8 amplified during the first PCR (926 bp DNA band 602); Lane 2 is the first fragment of SEQ ID NO: 7 amplified during the first PCR (1042 bp DNA band 604); Lane L2 is a 100 bp DNA ladder/marker; and Lane 3 is the second fragment of SEQ ID NO: 8 amplified through the first PCR (254 bp DNA band 606); and Lane 4 is the second fragment of SEQ ID NO: 7 amplified during the first PCR (147 bp DNA band 608).

Figure 6B:
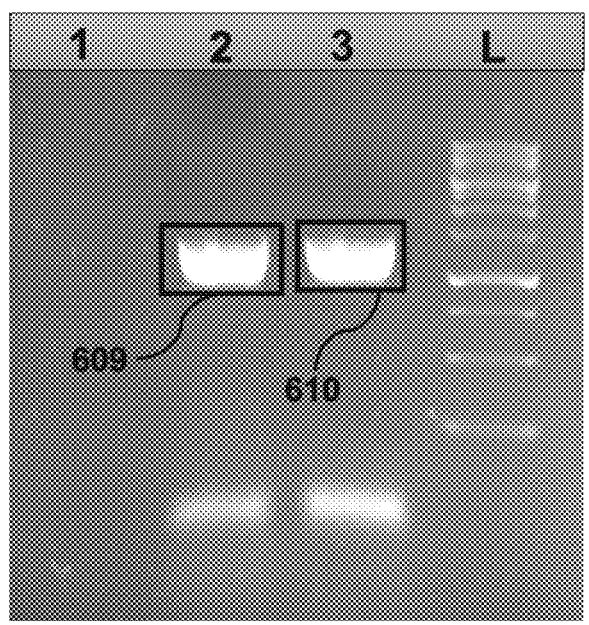
FIG. 6B shows agarose gel electrophoresis results of second PCR of the overlap PCR that results in amplification of entire sequence length of SEQ ID NOs: 7 and 8, consistent with exemplary embodiments of the present disclosure.

FIG. 6B illustrates agarose gel electrophoresis results of the second PCR of the overlap-PCR that results in amplification of the entire sequence length of SEQ ID NOs: 7 and 8, consistent with exemplary embodiments of the present disclosure. Referring to this figure, Lane 1 is a negative control lacking template DNA (i.e. the polynucleotides as set forth in SEQ ID NOs: 7 and 8); Lane 2 is the amplified SEQ ID NO: 8 amplified through the second PCR (1140 bp DNA band 609); Lane 3 is the amplified SEQ ID NO: 7 amplified through the second PCR (1140 bp DNA band 610); and Lane L is a 1 Kb DNA ladder/marker.

Example 3: Expression of the Truncated and Modified Serratiopeptidase

The nucleic acid sequence of SEQ ID NO: 6 was cloned in pET28a vector (Qiagen, Germany), and the nucleic acid sequences set forth in SEQ ID NOs: 7 and 8 were cloned in pQE30 vector. The generated recombinant constructs/vectors of pET28a and pQE30 were subsequently introduced into E. coli BL21(DE3)pLysS and E. coli M15, respectively. Then, recombinant clones were selected on LB (Luria-Bertani) agar plates containing kanamycin (25 µg/ml). Positive clones containing recombinant pET28a (having SEQ ID NO: 6) were confirmed by double digestion with restriction enzymes (NcoI and XhoI). Similarly, positive clones containing recombinant pQE30 (having SEQ ID NOs: 7 and 8) were confirmed by double digestion with restriction enzymes (BamHI and HindIII).

The obtained recombinant vectors were analyzed by electrophoresis on 1% agarose gel, and the cloned fragments (SEQ ID NO: 6, 7, and 8) were validated by sequencing.

Briefly, in order to introduce the recombinant vectors into E. coli BL21(DE3)pLysS and E. coli M15, a single colony of the bacteria carrying pET28a recombinant vector was added to 5 ml of LB broth containing kanamycin (25 µg/ml) and incubated at 37° C. (180 rpm, 18 to 24 h) until reaching an optical density (OD) of about 0.6-0.8 at 600 nm. Protein expression was induced by 0.5 mM isopropyl-β-D-thiogalactopyranoside (IPTG, Sigma, USA). The culture was further incubated for 4 h and the cells were harvested by centrifuging at 7,000 rpm for 15 min. Supernatant was discarded and pellet was kept at −20° C. for use in the future experiments. 1 ml of bacterial cultures were collected before and after IPTG induction for measuring bacterial growth (by measuring OD at 600 nm), and for analyzing the expressed protein by sodium dodecyl sulfate-polyacrylamide gel electrophoresis (SDS-PAGE, 12%). Expression of the truncated and modified Serratiopeptidase (100, 200, and/or 300) was confirmed by Western blotting (using antibody against polyhistidine) and by observing the protein band at the expected sizes (~35 kDa and 41 kDa).

Figure 7:
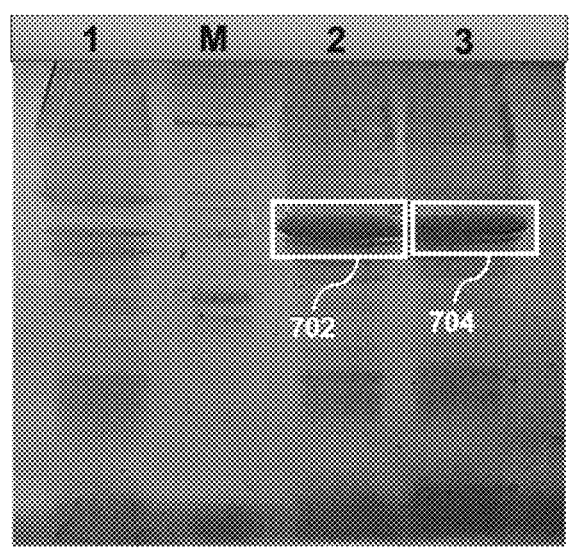
FIG. 7 shows SDS-PAGE analysis of transformed *E. coli* BL21 after expression of the truncated and modified Serratiopeptidase (SEQ ID NO: 2), consistent with one or more embodiments of the present disclosure.

FIG. 7 shows SDS-PAGE analysis of the transformed E. coli BL21 after expression of the truncated and modified Serratiopeptidase 100 (SEQ ID NO: 2), consistent with one or more embodiments of the present disclosure. The transformed E. coli BL21 may contain recombinant vectors harboring the polynucleotide set forth in SEQ ID NO: 6. As shown in FIG. 7, Lane M is a protein molecular weight marker (11-245 kDa); Lane 1 is the bacterial pellet before IPTG induction; Lane 2 is the bacterial pellet containing the recombinant vectors after 2 hours of IPTG induction; and Lane 3 is the bacterial pellet containing the recombinant vectors after 4 hours of IPTG induction. The SDS-PAGE analysis revealed a 35 kDa protein band 702 in Lane 2, and a 35 kDa protein band 704 in Lane 3.

Figure 8:
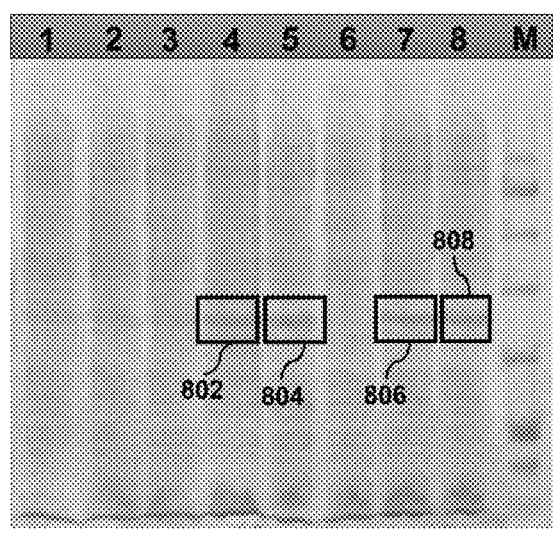
FIG. 8 shows SDS-PAGE analysis of transformed *E. coli* M15 after expression of the truncated and modified Serratiopeptidase (SEQ ID NOs: 3 and 4), consistent with one or more embodiments of the present disclosure.

FIG. 8 shows SDS-PAGE analysis of the transformed *E. coli* M15 after expression of the truncated and modified Serratiopeptidase 200 and 300 (SEQ ID NOs: 3 and 4), consistent with one or more embodiments of the present disclosure. The transformed *E. coli* M15 may contain recombinant vectors that harbor one of the polynucleotides set forth in SEQ ID NOs: 7 and 8. Referring to FIG. 8, Lane M is a protein molecular weight marker (11-245 kDa); Lane 1 is the bacterial pellet lacking the recombinant vectors (as negative control) before IPTG induction; Lane 2 is the bacterial pellet lacking the recombinant vectors (as negative control) after 4 h of IPTG induction; Lane 3 is the bacterial pellet containing the recombinant vectors expressing the truncated and modified Serratiopeptidase 200 (SEQ ID NO: 3) before induction; Lane 4 is the bacterial pellet containing the recombinant vectors expressing the truncated and modified Serratiopeptidase 200 (SEQ ID NO: 3) after 2 hours of induction; Lane 5 is the bacterial pellet containing the recombinant vectors expressing the truncated and modified Serratiopeptidase 200 (SEQ ID NO: 3) after 4 hours of induction; Lane 6 is the bacterial pellet containing the recombinant vectors expressing the truncated and modified Serratiopeptidase 300 (SEQ ID NO: 4) before induction; Lane 7 is the bacterial pellet containing the recombinant vectors expressing the truncated and modified Serratiopeptidase 300 (SEQ ID NO: 4) after 2 hours of induction; and Lane 8 is the bacterial pellet containing the recombinant vectors expressing the truncated and modified Serratiopeptidase 300 (SEQ ID NO: 4) after 4 hours of induction. The SDS-PAGE analysis of the transformed *E. coli* M15 revealed 41 kDa protein bands in Lane 4 (802), Lane 5 (804), Lane 7 (806), and Lane 8 (808).

Figure 9:
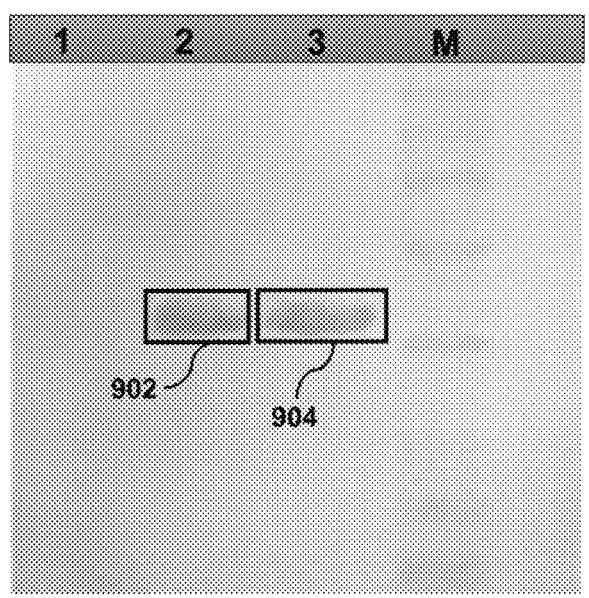
FIG. 9 shows western blot analysis of the truncated and modified Serratiopeptidase (SEQ ID NO: 2) after expression in transformed *E. coli* BL21, consistent with one or more embodiments of the present disclosure.

FIG. 9 shows western blot analysis of the truncated and modified Serratiopeptidase 100 (SEQ ID NO: 2) after expression in the transformed *E. coli* BL21, consistent with one or more embodiments of the present disclosure. As mentioned earlier, the transformed *E. coli* BL21 may contain recombinant vectors harboring the polynucleotide set forth in SEQ ID NO: 6. As shown in FIG. 9, Lane M is a protein molecular weight marker (11-245 kDa); Lane 1 is the bacterial pellet before IPTG induction; Lane 2 is the bacterial pellet after 2 hours of IPTG induction; and Lane 3 is the bacterial pellet after 4 hours of IPTG induction. The western blot analysis revealed 35 kDa protein bands in Lane 2 (902) and Lane 3 (904), proving that expression of the truncated and modified Serratiopeptidase 100 (SEQ ID NO: 2) may be at an optimum level after 2 or 4 hours of IPTG induction.

Figure 10:
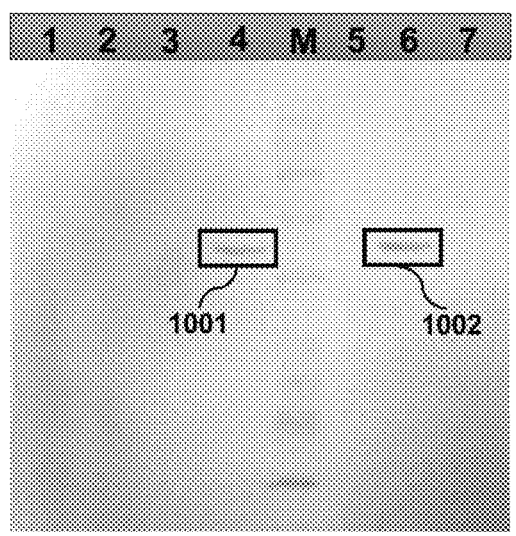
FIG. 10 shows western blot analysis of the truncated and modified Serratiopeptidase (SEQ ID NOs: 3 and 4) after expression in transformed *E. coli* M15, consistent with one or more embodiments of the present disclosure.

FIG. 10 shows western blot analysis of the truncated and modified Serratiopeptidase 200 and 300 (SEQ ID NOs: 3 and 4) after expression in the transformed *E. coli* M15, consistent with one or more embodiments of the present disclosure. As mentioned before, the transformed *E. coli* M15 may contain recombinant vectors harboring one of the polynucleotides set forth in SEQ ID NOs: 7 and 8. Lane M is a protein molecular weight marker (11-245 kDa); Lane 1 is the bacterial pellet lacking the recombinant vectors before IPTG induction; Lane 2 is the bacterial pellet lacking the recombinant vectors after 2 hours of IPTG induction; Lane 3 is the bacterial pellet lacking the recombinant vectors after 4 hours of IPTG induction; Lane 4 is the bacterial pellet containing the recombinant vectors expressing the truncated and modified Serratiopeptidase 200 (SEQ ID NO: 3) after 4 hours of IPTG induction; Lane 5 is the bacterial pellet containing the recombinant vectors expressing the truncated and modified Serratiopeptidase 200 (SEQ ID NO: 3) before IPTG induction; Lane 6 is the bacterial pellet containing the recombinant vectors expressing the truncated and modified Serratiopeptidase 300 (SEQ ID NO: 4) after 4 hours of IPTG induction; and Lane 7 is the bacterial pellet containing the recombinant vectors expressing the truncated and modified Serratiopeptidase 300 (SEQ ID NO: 4) before IPTG induction. Referring to FIG. 10, the western blot analysis revealed 41 kDa protein bands in Lane 4 (1001) and Lane 6 (1002).

Example 4: Extraction and Purification of the Truncated and Modified Serratiopeptidase Due to existence of 6 His-tag at the C-terminus of the truncated and modified Serratiopeptidase (100, 200, and 300), Nickel (Ni) column was employed for purification thereof. 10 ml of denaturing lysis buffer, potassium phosphate buffer, 150 mM NaCl and 10% of glycerol were used to re-suspend induced *E. coli* BL21 pellet and supernatant. The re-suspended cell pellet and supernatant were sonicated and the lysates were loaded on the Ni column. Washing steps were carried out using imidazole 15 mM, and the truncated and modified Serratiopeptidase (100, 200, and 300) were eluted with imidazole 500 mM. Finally, reductants were removed by dialysis in PBS buffer.

Figure 11:
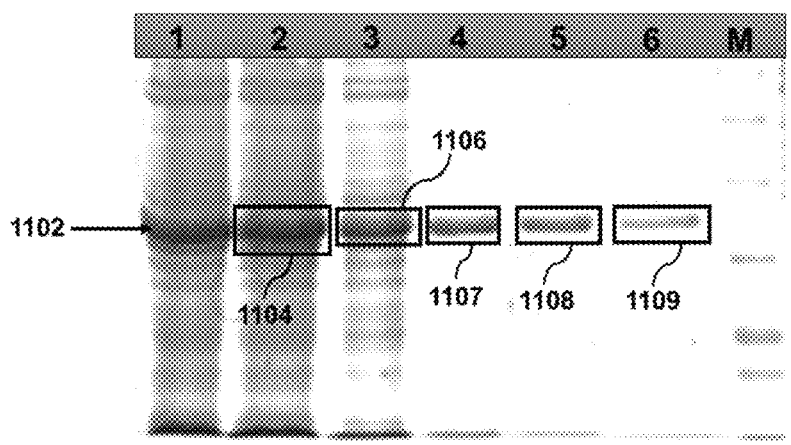
FIG. 11 shows SDS-PAGE analysis of the truncated and modified Serratiopeptidase (SEQ ID NO: 2) after expression in transformed *E. coli* BL21 and purification with affinity chromatography (Nickel column), consistent with one or more embodiments of the present disclosure.

FIG. 11 shows SDS-PAGE analysis of the truncated and modified Serratiopeptidase 100 (SEQ ID NO: 2) after expression in the transformed *E. coli* BL21 and purification with affinity chromatography (Nickel column), consistent with one or more embodiments of the present disclosure. Lane M is a protein molecular weight marker (11-245 kDa); Lane 1 is the bacterial lysate pellet after sonication; Lane 2 is supernatant of the centrifuged lysate; Lane 3 is a mixture of flow-through, first wash, and second wash eluted from the Nickel column; Lane 4 is a first fraction (10 µl) of the purified protein eluted from the Nickel column; Lane 5 is a second fraction (10 µl) of the purified protein eluted from the Nickel column; and Lane 6 is a third fraction (10 µl) of the purified protein eluted from the Nickel column. The SDS-PAGE analysis showed 35 kDa protein bands (1002, 1004, 1006, 1007, 1008, and 1009) in Lanes 1 to 6, respectively.

Figure 12:
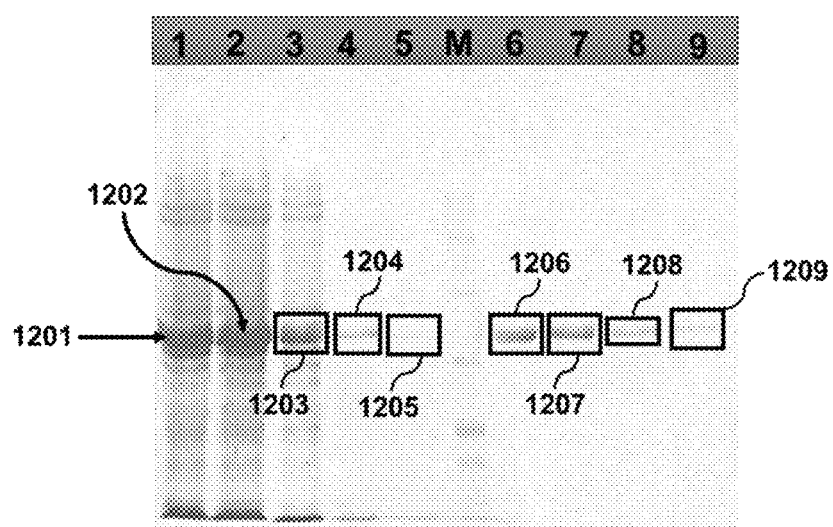
FIG. 12 shows SDS-PAGE analysis of the truncated and modified Serratiopeptidase (SEQ ID NO: 3) after expression in transformed *E. coli* M15 and purification with affinity chromatography (Nickel column), consistent with one or more embodiments of the present disclosure.

FIG. 12 shows SDS-PAGE analysis of the truncated and modified Serratiopeptidase 200 (SEQ ID NO: 3) after expression in transformed *E. coli* M15 and purification with affinity chromatography (Nickel column), consistent with one or more embodiments of the present disclosure. As shown in FIG. 12, Lane M is a protein molecular weight marker (11-245 kDa); Lane 1 is the bacterial lysate pellet after sonication; Lane 2 is supernatant of the centrifuged lysate; Lane 3 is a flow-through eluted from the Nickel column; Lane 4 is a first wash eluted from the Nickel column; Lane 5 is a second wash eluted from the Nickel column; Lane 6 is a first fraction (10 µl) of the purified protein eluted from the Nickel column; Lane 7 is a second fraction (10 µl) of the purified protein eluted from the Nickel column; Lane 8 is a third fraction (10 µl) of the purified protein eluted from the Nickel column; and Lane 9 is a fourth fraction (10 µl) of the purified protein eluted from the Nickel column. The SDS-PAGE analysis revealed 41 kDa protein bands (1201 to 1209) in Lanes 1 to 9, respectively.

Figure 13:
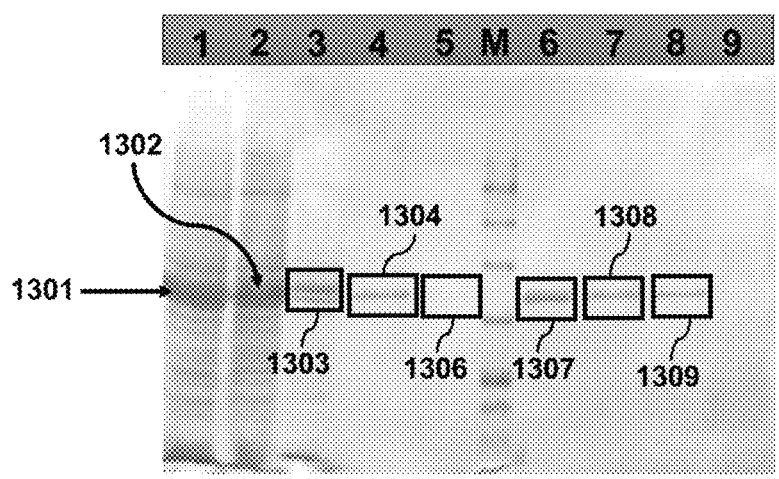
FIG. 13 shows SDS-PAGE analysis of the truncated and modified Serratiopeptidase (SEQ ID NO: 4) after expression in transformed *E. coli* M15 and purification with affinity chromatography (Nickel column), consistent with one or more embodiments of the present disclosure.

FIG. 13 shows SDS-PAGE analysis of the truncated and modified Serratiopeptidase 300 (SEQ ID NO: 4) after expression in transformed *E. coli* M15 and purification with affinity chromatography (Nickel column), consistent with one or more embodiments of the present disclosure. Lane M is a protein molecular weight marker (11-245 kDa); Lane 1 is bacterial lysate pellet after sonication; Lane 2 is supernatant of the centrifuged lysate; Lane 3 is a flow-through eluted from the Nickel column; Lane 4 is a first wash eluted from the Nickel column; Lane 5 is a second wash eluted from the Nickel column, Lane 6 is a first fraction (10 µl) of the purified protein eluted from the Nickel column; Lane 7 is a second fraction (10 µl) of the purified protein eluted from the Nickel column; Lane 8 is a third fraction (10 µl) of the purified protein eluted from the Nickel column; and Lane 9 is a fourth fraction (10 µl) of the purified protein eluted from the Nickel column. The SDS-PAGE analysis revealed 41 kDa protein bands (1301 to 1309) in Lanes 1 to 8, respectively.

Example 5: Evaluation of Enzymatic Activity

In this example, protease activity of the truncated and modified Serratiopeptidase (100, 200, and 300) was evaluated using casein as a substrate. In this assay, Tyrosine residue was released along with other amino acids and peptide fragments as a result of protease activity of the truncated and modified Serratiopeptidase 100, 200, and 300 (the protease/enzyme). To this end, a solution containing 150 µg/ml of the enzymes was prepared. Folin & Ciocalteus reagents were used for quantitative measurement of the enzymes; such reagents react with free Tyrosine to produce a blue colored chromophore, which is quantifiable and measured as an absorbance value on the spectrophotometer 660 nm. The enzyme's activity is directly proportional to the amount of Tyrosine released from casein. Absorbance values generated by activity of the protease were compared to a standard curve; the activity of protease samples may be determined based on the standard curve in terms of Units, which is the amount in micromoles of Tyrosine equivalents released from casein per minute.

Example 6: Evaluation of Enzyme Activity at Different Temperatures and pH

In this example, enzyme activity of the truncated and modified Serratiopeptidase (100, 200, and 300) was evaluated at pH values ranging from 6 to 9.5 and at different temperatures ranging from 25 to 90° C. using Universal Protease Activity Assay. The effect of temperature (evaluated from 25° C. to 90° C.) on the truncated and modified Serratiopeptidase (100, 200, and 300) activity was monitored using casein (0.65% w/v) as substrate. First, 5 mL of 0.65% casein solution (in 50 mM potassium phosphate buffer, w/v) was added to 15 mL vials. The solution was incubated in a water bath at 37° C. for about 5 minutes. Then, 200 µL of the truncated and modified Serratiopeptidase (100, 200, and 300) and the full-length Serratiopeptidase (PDB ID: 5D7W) with 150 µg/ml concentration was added to each of test vials. The enzyme solutions were incubated at 37° C. for 10 minutes (pH≈=7.5). After the 10-minute incubation, each of the test solutions were filtered using a 0.45 µm polyethersulfone syringe filter to remove any insolubles from the samples. Finally, 1 ml of 110 mM Trichloroacetic acid solution was added to each vial to stop the reaction. In fact, the protease activity is measured based on the releasing Tyrosine during this incubation time. Again, 200 µL of the truncated and modified Serratiopeptidase (100, 200, and 300) and the full-length Serratiopeptidase (PDB ID: 5D7W) with 150 µg/ml concentration was added to each of test and control vials; the enzyme solutions were incubated at 37° C. for 10 minutes (pH≈7.5). After the 30-minute incubation, each of the test and control solutions were filtered using a 0.45 µm polyethersulfone syringe filter. 1 mL of 500 mM Sodium carbonate solution and 1 of mL Folin's reagent (0.5 M) were added to all of the test and control vials, respectively. The vials (test and control) were mixed by swirling and incubated at 37° C. for 30 minutes. After the 30-minute incubation, the test and control solutions were analyzed at 660 nm using a spectrophotometer.

In order to evaluate the activity of enzyme in different pH values, the Universal Protease Activity Assay (casein assay) as discussed above was repeated at pH 6, 7.5, 8.5 and 9.5.

Table 1 and 2 below compare enzyme activity of the truncated and modified Serratiopeptidase 100, 200 and 300 (having SEQ ID NOs: 2, 3, and 4, respectively), with the full-length Serratiopeptidase presented in PDB ID: 5D7W at different pH values and temperatures.

The obtained results show that the truncated and modified Serratiopeptidase (100, 200 and 300) have more than 85%, 70%, and 75% residual activity at 90° C. after 10 minutes, respectively.

TABLE 1

Enzyme activity of the truncated and modified Serratiopeptidase 100, 200, and 300 (having SEQ ID NOs: 2, 3 and 4, respectively) and the full-length Serratiopeptidase (PDB ID: 5D7W) at 25 to 90° C. after 10 minutes.

| Serratiopeptidase | Temperature ° C. (Average OD 660 ± SD) | | | | |
|---|---|---|---|---|---|
| | 25 | 40 | 50 | 60 | 90 |
| PDB ID: 5D7W | 0.75 ± 0.8 | 0.61 ± 0.07 | 0.57 ± 0.08 | 0.41 ± 0.06 | 0.38 ± 0.05 |
| Serratiopeptidase 100 (SEQ ID NO: 2) | 1 ± 0.11 | 0.63 ± 0.09 | 0.74 ± 0.08 | 0.91 ± 0.09 | 0.87 ± 0.07 |
| Serratiopeptidase 200 (SEQ ID NO: 3) | 0.89 ± 0.12 | 0.47 ± 0.09 | 0.69 ± 0.07 | 0.79 ± 0.1 | 0.74 ± 0.07 |
| Serratiopeptidase 300 (SEQ ID NO: 4) | 0.81 ± 0.08 | 0.52 ± 0.13 | 0.75 ± 0.0.06 | 0.8 ± 0.09 | 0.78 ± 0.1 |

TABLE 2

Enzyme activity of the truncated and modified Serratiopeptidase 100, 200, and 300 (having SEQ ID NOs: 2, 3 and 4, respectively) and the full-length Serratiopeptidase (PDB ID: 5D7W) at pH values ranging from 6 to 9.5 after 10 minutes.

| Serratiopeptidase | pH (Average $OD_{660}$ ± SD) | | | |
|---|---|---|---|---|
| | 6 | 7.5 | 8.5 | 9.5 |
| PDB ID: 5D7W | 0.71 ± 0.06 | 0.83 ± 0.09 | 0.97 ± 0.1 | 0.92 ± 0.11 |
| Serratiopeptidase 100 (SEQ ID NO: 2) | 0.97 ± 0.12 | 1.11 ± 0.13 | 1.34 ± 0.15 | 1.29 ± 0.12 |
| Serratiopeptidase 200 (SEQ ID NO: 3) | 0.81 ± 0.12 | 0.94 ± 0.12 | 1.15 ± 0.12 | 1.04 ± 0.12 |
| Serratiopeptidase 300 (SEQ ID NO: 4) | 0.64 ± 0.12 | 0.78 ± 0.12 | 1.03 ± 0.12 | 0.96 ± 0.12 |

Example 7: Evaluation of Anti-Biofilm Activity

In this example, ability of the truncated and modified Serratiopeptidase (100, 200, and 300) for inhibiting biofilm formation and growth of *Staphylococcus aureus* and *Pseudomonas aeruginosa* was investigated.

Bacterial growth and biofilm formation in the presence and absence of the truncated and modified Serratiopeptidase (100, 200, and 300) were measured by spectrophotometer at 550 nm. Table 3 below, presents the effect of the truncated and modified Serratiopeptidase (100, 200, and 300) on *Staphylococcus aureus*' and *Pseudomonas aeruginosa*'s growth.

TABLE 3

Bacterial growth of *Staphylococcus aureus* and *Pseudomonas aeruginosa* in the presence of the truncated and modified Serratiopeptidase 100, 200, and 300 (having SEQ ID NOs: 2, 3, and 4, respectively) and the full-length Serratiopeptidase (PDB ID: 5D7W).

| Serratiopeptidase | Bacterial growth (Average $OD_{550}$ ± SD) | |
|---|---|---|
| PDB ID: 5D7W | 0.514 ± 0.09 | 0.311 ± 0.07 |
| Serratiopeptidase 100 (SEQ ID NO: 2) | 0.224 ± 0.06 | 0.126 ± 0.05 |
| Serratiopeptidase 200 (SEQ ID NO: 3) | 0.302 ± 0.07 | 0.183 ± 0.06 |
| Serratiopeptidase 300 (SEQ ID NO: 4) | 0.423 ± 0.08 | 0.214 ± 0.06 |
| Control (bacterial growth in the absence of Serratiopeptidase) | 1.106 ± 0.11 | 0.502 ± 0.09 |

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. An element proceeded by "a" or "an" does not, without further constraints, preclude the existence of additional identical elements in the process, method, article, or apparatus that comprises the element.

Unless otherwise stated, all measurements, values, ratings, positions, magnitudes, sizes, and other specifications that are set forth in this specification, are approximate, not exact. They are intended to have a reasonable range that is consistent with the functions to which they relate and with what is customary in the art to which they pertain.

It will be understood that the terms and expressions used herein have the ordinary meaning as is accorded to such terms and expressions with respect to their corresponding respective areas of inquiry and study, except where specific meanings have otherwise been set forth herein. Relational terms such as "first" and "second" and the like may be used solely to distinguish one entity or action from another without necessarily requiring or implying any actual such relationship or order between such entities or actions.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it may be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

```
                          SEQUENCE LISTING

<160> NUMBER OF SEQ ID NOS: 22

<210> SEQ ID NO 1
<211> LENGTH: 471
<212> TYPE: PRT
<213> ORGANISM: Serratia marcescens
<220> FEATURE:
<221> NAME/KEY: VARIANT
<222> LOCATION: (1)..(471)
<300> PUBLICATION INFORMATION:
<308> DATABASE ACCESSION NUMBER: NCBI/WP_021504810
<309> DATABASE ENTRY DATE: 2020-05-11
<313> RELEVANT RESIDUES IN SEQ ID NO: (1)..(471)

<400> SEQUENCE: 1

Ala Ala Ala Thr Gly Tyr Asp Ala Val Asp Leu Leu His Tyr His
1               5                   10                  15

Glu Arg Gly Asn Gly Ile Gln Ile Asn Gly Lys Asp Ser Phe Ser Asn
                20                  25                  30

Glu Gln Ala Gly Leu Phe Ile Thr Arg Glu Asn Gln Thr Trp Asn Gly
            35                  40                  45

Tyr Lys Val Phe Gly Gln Pro Val Lys Leu Thr Phe Ser Phe Pro Asp
    50                  55                  60

Tyr Lys Phe Ser Ser Thr Asn Val Ala Gly Asp Thr Gly Leu Ser Lys
65                  70                  75                  80

Phe Ser Ala Glu Gln Gln Gln Gln Ala Lys Leu Ser Leu Gln Ser Trp
                85                  90                  95

Ala Asp Val Ala Asn Ile Thr Phe Thr Glu Val Ala Ala Gly Gln Lys
            100                 105                 110

Ala Asn Ile Thr Phe Gly Asn Tyr Ser Gln Asp Arg Pro Gly His Tyr
        115                 120                 125

Asp Tyr Gly Thr Gln Ala Tyr Ala Phe Leu Pro Asn Thr Ile Trp Gln
    130                 135                 140

Gly Gln Asp Leu Gly Gly Gln Thr Trp Tyr Asn Val Asn Gln Ser Asn
145                 150                 155                 160

Val Lys His Pro Ala Thr Glu Asp Tyr Gly Arg Gln Thr Phe Thr His
                165                 170                 175

Glu Ile Gly His Ala Leu Gly Leu Ser His Pro Gly Asp Tyr Asn Ala
            180                 185                 190

Gly Glu Gly Asn Pro Thr Tyr Asn Asp Val Thr Tyr Ala Glu Asp Thr
        195                 200                 205

Arg Gln Phe Ser Leu Met Ser Tyr Trp Ser Glu Thr Asn Thr Gly Gly
    210                 215                 220

Asp Asn Gly Gly His Tyr Ala Ala Ala Pro Leu Leu Asp Asp Ile Ala
225                 230                 235                 240
```

-continued

```
Ala Ile Gln His Leu Tyr Gly Ala Asn Leu Ser Thr Arg Thr Gly Asp
            245                 250                 255

Thr Val Tyr Gly Phe Asn Ser Asn Thr Gly Arg Asp Phe Leu Ser Thr
        260                 265                 270

Thr Ser Asn Ser Gln Lys Val Ile Phe Ala Ala Trp Asp Ala Gly Gly
    275                 280                 285

Asn Asp Thr Phe Asp Phe Ser Gly Tyr Thr Ala Asn Gln Arg Ile Asn
290                 295                 300

Leu Asn Glu Lys Ser Phe Ser Asp Val Gly Leu Lys Gly Asn Val
305                 310                 315                 320

Ser Ile Ala Ala Gly Val Thr Ile Glu Asn Ala Ile Gly Gly Ser Gly
                325                 330                 335

Asn Asp Val Ile Val Gly Asn Ala Ala Asn Asn Val Leu Lys Gly Gly
            340                 345                 350

Ala Gly Asn Asp Val Leu Phe Gly Gly Gly Ala Asp Glu Leu Trp
        355                 360                 365

Gly Gly Ala Gly Lys Asp Ile Phe Val Phe Ser Ala Ala Ser Asp Ser
370                 375                 380

Ala Pro Gly Ala Ser Asp Trp Ile Arg Asp Phe Gln Lys Gly Ile Asp
385                 390                 395                 400

Lys Ile Asp Leu Ser Phe Phe Asn Lys Glu Ala Asn Ser Ser Asp Phe
                405                 410                 415

Ile His Phe Val Asp His Phe Ser Gly Thr Ala Gly Glu Ala Leu Leu
            420                 425                 430

Ser Tyr Asn Ala Ser Ser Asn Val Thr Asp Leu Ser Val Asn Ile Gly
        435                 440                 445

Gly His Gln Ala Pro Asp Phe Leu Val Lys Ile Val Gly Gln Val Asp
    450                 455                 460

Val Ala Thr Asp Phe Ile Val
465                 470

<210> SEQ ID NO 2
<211> LENGTH: 344
<212> TYPE: PRT
<213> ORGANISM: Unknown
<220> FEATURE:
<223> OTHER INFORMATION: Truncated and modified Serratiopeptidase
      designed based on SEQ ID NO: 1; Expressed in Escherichia coli BL21

<400> SEQUENCE: 2

Ala Ala Ala Thr Gly Tyr Asp Cys Val Asp Asp Leu Leu His Tyr His
1               5                   10                  15

Glu Arg Gly Asn Gly Ile Gln Ile Asn Gly Lys Asp Ser Phe Ser Asn
            20                  25                  30

Glu Gln Ala Gly Leu Phe Ile Thr Arg Glu Asn Gln Thr Trp Asn Gly
        35                  40                  45

Tyr Lys Val Phe Gly Gln Pro Val Lys Leu Thr Phe Ser Phe Pro Asp
    50                  55                  60

Tyr Lys Phe Ser Ser Thr Asn Val Ala Gly Asp Thr Gly Leu Ser Lys
65                  70                  75                  80

Phe Ser Ala Glu Gln Gln Gln Ala Lys Leu Ser Leu Gln Ser Trp
                85                  90                  95

Ala Asp Val Ala Asn Ile Thr Phe Thr Glu Val Ala Ala Gly Gln Lys
            100                 105                 110

Ala Asn Ile Thr Phe Gly Asn Tyr Ser Gln Asp Arg Pro Gly His Tyr
        115                 120                 125
```

Asp Tyr Gly Thr Gln Ala Tyr Ala Phe Leu Pro Asn Thr Ile Trp Gln
            130                 135                 140

Gly Gln Asp Leu Gly Gly Gln Thr Trp Tyr Asn Val Asn Gln Ser Asn
145                 150                 155                 160

Val Lys His Pro Ala Thr Glu Asp Tyr Gly Arg Gln Thr Phe Thr His
                165                 170                 175

Glu Ile Gly His Ala Leu Gly Leu Ser His Pro Gly Asp Tyr Asn Ala
            180                 185                 190

Gly Glu Gly Asn Pro Thr Tyr Asn Asp Val Thr Tyr Ala Glu Asp Thr
        195                 200                 205

Arg Gln Phe Ser Leu Met Ser Tyr Trp Ser Glu Thr Asn Thr Gly Gly
210                 215                 220

Asp Asn Gly Gly His Tyr Ala Ala Pro Leu Leu Asp Asp Ile Ala
225                 230                 235                 240

Ala Ile Gln His Leu Tyr Gly Ala Asn Leu Ser Thr Arg Thr Gly Asp
                245                 250                 255

Thr Val Tyr Gly Phe Asn Ser Asn Thr Gly Arg Asp Phe Leu Ser Thr
            260                 265                 270

Thr Ser Asn Ser Gln Lys Val Ile Phe Ala Ala Trp Asp Ala Gly Gly
        275                 280                 285

Asn Asp Thr Phe Asp Phe Ser Gly Tyr Thr Ala Asn Gln Arg Ile Asn
290                 295                 300

Leu Asn Glu Lys Ser Phe Ser Asp Val Gly Gly Leu Lys Gly Asn Val
305                 310                 315                 320

Ser Ile Ala Ala Gly Val Thr Ile Glu Asn Ala Ile Gly Gly Ser Gly
                325                 330                 335

Asn Asp Cys Ile Val Gly Asn Ala
            340

<210> SEQ ID NO 3
<211> LENGTH: 380
<212> TYPE: PRT
<213> ORGANISM: Unknown
<220> FEATURE:
<223> OTHER INFORMATION: Truncated and modified Serratiopeptidase
      designed based on SEQ ID NO: 1; Expressed in Escherichia coli M15

<400> SEQUENCE: 3

Ala Ala Ala Thr Gly Tyr Asp Cys Val Asp Asp Leu Leu His Tyr His
1               5                   10                  15

Glu Arg Gly Asn Gly Ile Gln Ile Asn Gly Lys Asp Ser Phe Ser Asn
            20                  25                  30

Glu Gln Ala Gly Leu Phe Ile Thr Arg Glu Asn Gln Thr Trp Asn Gly
        35                  40                  45

Tyr Lys Val Phe Gly Gln Pro Val Lys Leu Thr Phe Ser Phe Pro Asp
50                  55                  60

Tyr Lys Phe Ser Ser Thr Asn Val Ala Gly Asp Thr Gly Leu Ser Lys
65                  70                  75                  80

Phe Ser Ala Glu Gln Gln Gln Gln Ala Lys Leu Ser Leu Gln Ser Trp
                85                  90                  95

Ala Asp Val Ala Asn Ile Thr Phe Thr Glu Val Ala Ala Gly Gln Lys
            100                 105                 110

Ala Asn Ile Thr Phe Gly Asn Tyr Ser Gln Asp Arg Pro Gly His Tyr
        115                 120                 125

Asp Tyr Gly Thr Gln Ala Tyr Ala Phe Leu Pro Asn Thr Ile Trp Gln

```
                    130                 135                 140
Gly Gln Asp Leu Gly Gly Gln Thr Trp Tyr Asn Val Asn Gln Ser Asn
145                 150                 155                 160

Val Lys His Pro Ala Thr Glu Asp Tyr Gly Arg Gln Thr Phe Thr His
                165                 170                 175

Glu Ile Gly His Ala Leu Gly Leu Ser His Pro Gly Asp Tyr Asn Ala
                180                 185                 190

Gly Glu Gly Asn Pro Thr Tyr Asn Asp Val Thr Tyr Ala Glu Asp Thr
            195                 200                 205

Arg Gln Phe Ser Leu Met Ser Tyr Trp Ser Glu Thr Asn Thr Gly Gly
            210                 215                 220

Asp Asn Gly Gly His Tyr Ala Ala Ala Pro Leu Leu Asp Asp Ile Ala
225                 230                 235                 240

Ala Ile Gln His Leu Tyr Gly Ala Asn Leu Ser Thr Arg Thr Gly Asp
                245                 250                 255

Thr Val Tyr Gly Phe Asn Ser Asn Thr Gly Arg Asp Phe Leu Ser Thr
            260                 265                 270

Thr Ser Asn Ser Gln Lys Val Ile Phe Ala Ala Trp Asp Ala Gly Gly
            275                 280                 285

Asn Asp Thr Phe Asp Phe Ser Gly Tyr Thr Ala Asn Gln Arg Ile Asn
290                 295                 300

Leu Asn Glu Lys Ser Phe Ser Asp Val Gly Gly Leu Lys Gly Asn Val
305                 310                 315                 320

Ser Ile Ala Ala Gly Val Thr Ile Glu Asn Ala Ile Gly Gly Ser Gly
                325                 330                 335

Asn Asp Cys Ile Val Gly Asn Ala Ala Asn Asn Val Leu Lys Gly Gly
                340                 345                 350

Ala Gly Asn Asp Val Leu Phe Gly Gly Gly Gly Ala Asp Glu Leu Trp
            355                 360                 365

Gly Gly Ala Gly Lys Asp Ile Phe Val Phe Ser Ala
            370                 375                 380

<210> SEQ ID NO 4
<211> LENGTH: 380
<212> TYPE: PRT
<213> ORGANISM: Unknown
<220> FEATURE:
<223> OTHER INFORMATION: Truncated and modified Serratiopeptidase
      designed based on SEQ ID NO: 1; Expressed in Escherichia coli M15

<400> SEQUENCE: 4

Ala Ala Ala Thr Gly Tyr Asp Ala Val Asp Asp Cys Leu His Tyr His
1               5                   10                  15

Glu Arg Gly Asn Gly Ile Gln Ile Asn Gly Lys Asp Ser Phe Ser Asn
                20                  25                  30

Glu Gln Ala Gly Leu Phe Ile Thr Arg Glu Asn Gln Thr Trp Asn Gly
            35                  40                  45

Tyr Lys Val Phe Gly Gln Pro Val Lys Leu Thr Ser Phe Pro Asp
        50                  55                  60

Tyr Lys Phe Ser Ser Thr Asn Val Ala Gly Asp Thr Gly Leu Ser Lys
65                  70                  75                  80

Phe Ser Ala Glu Gln Gln Gln Ala Lys Leu Ser Leu Gln Ser Trp
                85                  90                  95

Ala Asp Val Ala Asn Ile Thr Phe Thr Glu Val Ala Ala Gly Gln Lys
                100                 105                 110
```

Ala Asn Ile Thr Phe Gly Asn Tyr Ser Gln Asp Arg Pro Gly His Tyr
            115                 120                 125

Asp Tyr Gly Thr Gln Ala Tyr Ala Phe Leu Pro Asn Thr Ile Trp Gln
        130                 135                 140

Gly Gln Asp Leu Gly Gly Gln Thr Trp Tyr Asn Val Asn Gln Ser Asn
145                 150                 155                 160

Val Lys His Pro Ala Thr Glu Asp Tyr Gly Arg Gln Thr Phe Thr His
                165                 170                 175

Glu Ile Gly His Ala Leu Gly Leu Ser His Pro Gly Asp Tyr Asn Ala
            180                 185                 190

Gly Glu Gly Asn Pro Thr Tyr Asn Asp Val Thr Tyr Ala Glu Asp Thr
        195                 200                 205

Arg Gln Phe Ser Leu Met Ser Tyr Trp Ser Glu Thr Asn Thr Gly Gly
210                 215                 220

Asp Asn Gly Gly His Tyr Ala Ala Ala Pro Leu Leu Asp Asp Ile Ala
225                 230                 235                 240

Ala Ile Gln His Leu Tyr Gly Ala Asn Leu Ser Thr Arg Thr Gly Asp
                245                 250                 255

Thr Val Tyr Gly Phe Asn Ser Asn Thr Gly Arg Asp Phe Leu Ser Thr
            260                 265                 270

Thr Ser Asn Ser Gln Lys Val Ile Phe Ala Ala Trp Asp Ala Gly Gly
        275                 280                 285

Asn Asp Thr Phe Asp Phe Ser Gly Tyr Thr Ala Asn Gln Cys Ile Asn
        290                 295                 300

Leu Asn Glu Lys Ser Phe Ser Asp Val Gly Gly Leu Lys Gly Asn Val
305                 310                 315                 320

Ser Ile Ala Ala Gly Val Thr Ile Glu Asn Ala Ile Gly Gly Ser Gly
                325                 330                 335

Asn Asp Val Ile Val Gly Asn Ala Ala Asn Asn Val Leu Lys Gly Gly
            340                 345                 350

Ala Gly Asn Asp Val Leu Phe Gly Gly Gly Ala Asp Glu Leu Trp
        355                 360                 365

Gly Gly Ala Gly Lys Asp Ile Phe Val Phe Ser Ala
370                 375                 380

<210> SEQ ID NO 5
<211> LENGTH: 1413
<212> TYPE: DNA
<213> ORGANISM: Artificial Sequence
<220> FEATURE:
<223> OTHER INFORMATION: Modified and codon-optimized polynucleotide
    designed based on a gene derived from Serratia marcescens that
    encodes for "serralysin family metalloprotease"; Produced
    synthetically; Codon-optimized based on Escherichia coli
    expression system

<400> SEQUENCE: 5
gcggcggcga ccggctacga cgcggttgac gacctgctgc actatcacga acgcggcaat      60
ggtatccaga ttaacggcaa ggacagcttc agcaacgagc aggcgggtct gtttatcacc     120
cgtgaaaacc aaacctggaa cggttacaag gtgtttggcc agccggttaa actgaccttc     180
agctttccgg actataagtt cagcagcacc aacgtggcgg tgataccgg cctgagcaag     240 tttagcgcgg agcagcaaca gcaagcgaaa ctgagcctgc agagctgggc ggatgtggcg     300
aacatcacct tcaccgaagt tgcggcgggt caaaaagcga acattacctt tggcaactac     360
agccaggacc gtccgggtca ctacgattat ggcacccaag cgtatgcgtt cctgccgaac     420

-continued

```
accatctggc agggtcaaga cctgggtggc cagacctggt acaacgtgaa ccaaagcaac      480
gttaagcacc cggcgaccga ggattatggt cgtcagacct ttacccacga aattggtcat      540
gcgctgggcc tgagccatcc gggtgactac aacgcgggcg agggcaaccc gacctacaac      600
gacgtgacct atgcggaaga tacccgtcag ttcagcctga tgagctactg gagcgaaacc      660
aacaccggtg gcgataacgg tggccactat gcggcggcgc cgctgctgga cgatattgcg      720
gcgattcaac acctgtacgg tgcgaacctg agcacccgta ccggtgacac cgtgtatggc      780
ttcaacagca acaccggtcg tgattttctg agcaccacca gcaacagcca gaaagttatc      840
tttgcggcgt gggatgcggg tggcaacgac accttcgatt ttagcggtta taccgcgaac      900
caacgtatta acctgaacga gaagagcttt agcgatgttg gtggcctgaa gggtaacgtg      960
agcatcgcgg cgggcgttac catcgaaaac gcgattggtg gcagcggtaa cgacgtgatt     1020
gtaggcaacg cggcgaacaa cgtgctgaag ggtggcgcgg gtaacgacgt tctgtttggt     1080
ggcggtggcg cggatgaact gtggggtggc gcgggtaaag acatcttcgt gtttagcgcg     1140
gcgagcgata gcgcgccggg tgcgagcgac tggattcgta tttccagaa gggcatcgac     1200 aaaattgatc tgagcttctt taacaaagag gcgaacagca gcgacttcat ccactttgtt     1260
gatcacttta gcgtaccgc gggtgaagcg ctgctgagct acaacgcgag cagcaacgtg     1320
accgacctga gcgttaacat tggtggccac caagcgccgg attttctggt gaagattgtg     1380
ggtcaggtgg atgttgcgac cgactttatc gtt                                  1413
```

<210> SEQ ID NO 6
<211> LENGTH: 1032
<212> TYPE: DNA
<213> ORGANISM: Artificial Sequence
<220> FEATURE:
<223> OTHER INFORMATION: Modified polynucleotide designed based on SEQ
      ID NO: 5 that encodes for the truncated and modified
      Serratiopeptidase set forth in SEQ ID NO: 2; Produced by
      PCR-amplification of SEQ ID NO: 5 using specific primers set forth
      in SEQ ID NOs: 9 and 10

<400> SEQUENCE: 6

```
gcggcggcga ccggctacga ctgcgttgac gacctgctgc actatcacga acgcggcaat       60
ggtatccaga ttaacggcaa ggacagcttc agcaacgagc aggcgggtct gtttatcacc      120
cgtgaaaacc aaacctggaa cggttacaag gtgtttggcc agccggttaa actgaccttc      180
agctttccgg actataagtt cagcagcacc aacgtggcgg gtgataccgg cctgagcaag      240
tttagcgcgg agcagcaaca gcaagcgaaa ctgagcctgc agagctgggc ggatgtggcg      300
aacatcacct tcaccgaagt tgcggcgggt caaaaagcga acattacctt tggcaactac      360
agccaggacc gtccgggtca ctacgattat ggcacccaag cgtatgcgtt cctgccgaac      420
accatctggc agggtcaaga cctgggtggc cagacctggt acaacgtgaa ccaaagcaac      480
gttaagcacc cggcgaccga ggattatggt cgtcagacct ttacccacga aattggtcat      540
gcgctgggcc tgagccatcc gggtgactac aacgcgggcg agggcaaccc gacctacaac      600
gacgtgacct atgcggaaga tacccgtcag ttcagcctga tgagctactg gagcgaaacc      660
aacaccggtg gcgataacgg tggccactat gcggcggcgc cgctgctgga cgatattgcg      720
gcgattcaac acctgtacgg tgcgaacctg agcacccgta ccggtgacac cgtgtatggc      780
ttcaacagca acaccggtcg tgattttctg agcaccacca gcaacagcca gaaagttatc      840
tttgcggcgt gggatgcggg tggcaacgac accttcgatt ttagcggtta taccgcgaac      900
caacgtatta acctgaacga gaagagcttt agcgatgttg gtggcctgaa gggtaacgtg      960
```

```
agcatcgcgg cgggcgttac catcgaaaac gcgattggtg gcagcggtaa cgactgcatt    1020
gtaggcaacg cg                                                        1032
```

<210> SEQ ID NO 7
<211> LENGTH: 1140
<212> TYPE: DNA
<213> ORGANISM: Artificial Sequence
<220> FEATURE:
<223> OTHER INFORMATION: Modified polynucleotide designed based on SEQ
      ID NO: 5 that encodes for the truncated and modified
      Serratiopeptidase set forth in SEQ ID NO: 3; Produced by overlap
      PCR of SEQ ID NO: 5 using specific primers set forth in SEQ ID
      NOs: 11 through 16

<400> SEQUENCE: 7

```
gcggcggcga ccggctacga ctgcgttgac gacctgctgc actatcacga acgcggcaat     60
ggtatccaga ttaacggcaa ggacagcttc agcaacgagc aggcgggtct gtttatcacc    120
cgtgaaaacc aaacctggaa cggttacaag gtgtttggcc agccggttaa actgaccttc    180
agctttccgg actataagtt cagcagcacc aacgtggcgg gtgataccgg cctgagcaag    240
tttagcgcgg agcagcaaca gcaagcgaaa ctgagcctgc agagctgggc ggatgtggcg    300
aacatcacct tcaccgaagt tgcggcgggt caaaaagcga acattacctt ggcaactac     360 agccaggacc gtccgggtca ctacgattat ggcacccaag cgtatgcgtt cctgccgaac    420
accatctggc agggtcaaga cctgggtggc cagacctggt acaacgtgaa ccaaagcaac    480
gttaagcacc cggcgaccga ggattatggt cgtcagacct ttacccacga aattggtcat    540
gcgctgggcc tgagccatcc gggtgactac aacgcgggcg agggcaaccc gacctacaac    600
gacgtgacct atgcggaaga tacccgtcag ttcagcctga tgagctactg gagcgaaacc    660
aacaccggtg gcgataacgg tggccactat gcggcggcgc cgctgctgga cgatattgcg    720
gcgattcaac acctgtacgg tgcgaacctg agcacccgta ccggtgacac cgtgtatggc    780
ttcaacagca acaccggtcg tgattttctg agcaccacca gcaacagcca gaaagttatc    840
tttgcggcgt gggatgcggg tggcaacgac accttcgatt ttagcggtta taccgcgaac    900
caacgtatta acctgaacga aagagcttt agcgatgttg gtggcctgaa gggtaacgtg    960
agcatcgcgg cgggcgttac catcgaaaac gcgattggtg gcagcggtaa cgactgcatt    1020
gtaggcaacg cggcgaacaa cgtgctgaag ggtggcgcgg gtaacgacgt tctgttttggt    1080 ggcggtggcg cggatgaact gtggggtggc gcgggtaaag acatcttcgt gtttagcgcg    1140
```

<210> SEQ ID NO 8
<211> LENGTH: 1140
<212> TYPE: DNA
<213> ORGANISM: Artificial Sequence
<220> FEATURE:
<223> OTHER INFORMATION: Modified polynucleotide designed based on SEQ
      ID NO: 5 that encodes for the truncated and modified
      Serratiopeptidase set forth in SEQ ID NO: 4; Produced by overlap
      PCR of SEQ ID NO: 5 using specific primers set forth in SEQ ID
      NOs: 17 through 22

<400> SEQUENCE: 8

```
gcggcggcga ccggctacga cgcggttgac gactgcctgc actatcacga acgcggcaat     60
ggtatccaga ttaacggcaa ggacagcttc agcaacgagc aggcgggtct gtttatcacc    120
cgtgaaaacc aaacctggaa cggttacaag gtgtttggcc agccggttaa actgaccttc    180
agctttccgg actataagtt cagcagcacc aacgtggcgg gtgataccgg cctgagcaag    240
```

```
tttagcgcgg agcagcaaca gcaagcgaaa ctgagcctgc agagctgggc ggatgtggcg      300
aacatcacct tcaccgaagt tgcggcgggt caaaaagcga acattacctt tggcaactac      360
agccaggacc gtccgggtca ctacgattat ggcacccaag cgtatgcgtt cctgccgaac      420
accatctggc agggtcaaga cctgggtggc cagacctggt acaacgtgaa ccaaagcaac      480
gttaagcacc cggcgaccga ggattatggt cgtcagacct ttacccacga aattggtcat      540
gcgctgggcc tgagccatcc gggtgactac aacgcgggcg agggcaaccc gacctacaac      600
gacgtgacct atgcggaaga tacccgtcag ttcagcctga tgagctactg gagcgaaacc      660
aacaccggtg gcgataacgg tggccactat gcggcggcgc cgctgctgga cgatattgcg      720
gcgattcaac acctgtacgg tgcgaacctg agcacccgta ccggtgacac cgtgtatggc      780
ttcaacagca acaccggtcg tgattttctg agcaccacca gcaacagcca gaaagttatc      840
tttgcggcgt gggatgcggg tggcaacgac accttcgatt ttagcggtta taccgcgaac      900
caatgcatta acctgaacga gaagagcttt agcgatgttg gtggcctgaa gggtaacgtg      960
agcatcgcgg cgggcgttac catcgaaaac gcgattggtg gcagcggtaa cgacgtgatt      1020
gtaggcaacg cggcgaacaa cgtgctgaag ggtggcgcgg gtaacgacgt tctgtttggt      1080
ggcggtggcg cggatgaact gtggggtggc gcgggtaaag acatcttcgt gtttagcgcg      1140
```

<210> SEQ ID NO 9
<211> LENGTH: 49
<212> TYPE: DNA
<213> ORGANISM: Artificial Sequence
<220> FEATURE:
<223> OTHER INFORMATION: Forward primer for amplifying SEQ ID NO: 6,
      using SEQ ID NO: 5 as template

<400> SEQUENCE: 9
catgccatgg cggcggcgac cggctacgac tgcgttgacg acctgctgc                   49

<210> SEQ ID NO 10
<211> LENGTH: 52
<212> TYPE: DNA
<213> ORGANISM: Artificial Sequence
<220> FEATURE:
<223> OTHER INFORMATION: Reverse primer for amplifying SEQ ID NO: 6,
      using SEQ ID NO: 5 as template

<400> SEQUENCE: 10
accgctcgag cgcgttgcct acaatacagt cgttaccgct gccaccaatc gc               52

<210> SEQ ID NO 11
<211> LENGTH: 52
<212> TYPE: DNA
<213> ORGANISM: Artificial Sequence
<220> FEATURE:
<223> OTHER INFORMATION: Forward primer for amplifying a first fragment
      of SEQ ID NO: 7 in a first PCR of an overlap PCR, and for
      introducing a TGC mutation thereto, wherein the template is SEQ ID
      NO: 5

<400> SEQUENCE: 11
acgggatcca tggcggcggc gaccggctac gactgcgttg acgacctgct gc               52

<210> SEQ ID NO 12
<211> LENGTH: 55
<212> TYPE: DNA
<213> ORGANISM: Artificial Sequence
<220> FEATURE:
<223> OTHER INFORMATION: Reverse primer for amplifying the first
      fragment of SEQ ID NO: 7 in the first PCR of the overlap PCR, and

```
      for introducing a ACA mutation thereto, wherein the template is
      SEQ ID NO: 5

<400> SEQUENCE: 12
cagcacgttg ttcgccgcgt tgcctacaat acagtcgtta ccgctgccac caatc         55

<210> SEQ ID NO 13
<211> LENGTH: 47
<212> TYPE: DNA
<213> ORGANISM: Artificial Sequence
<220> FEATURE:
<223> OTHER INFORMATION: Forward primer for amplifying a second fragment
      of SEQ ID NO: 7 in the first PCR of the overlap PCR, and for
      introducing a TGT mutation thereto, wherein the template is SEQ ID
      NO: 5

<400> SEQUENCE: 13
cgattggtgg cagcggtaac gactgtattg taggcaacgc ggcgaac                  47

<210> SEQ ID NO 14
<211> LENGTH: 31
<212> TYPE: DNA
<213> ORGANISM: Artificial Sequence
<220> FEATURE:
<223> OTHER INFORMATION: Reverse primer for amplifying the second
      fragment of SEQ ID NO: 7 in the first PCR of the overlap PCR,
      wherein the template is SEQ ID NO: 5

<400> SEQUENCE: 14
acccaagctt cgcgctaaac acgaagatgt c                                   31

<210> SEQ ID NO 15
<211> LENGTH: 52
<212> TYPE: DNA
<213> ORGANISM: Artificial Sequence
<220> FEATURE:
<223> OTHER INFORMATION: Forward primer for amplifynig entire sequence
      of SEQ ID NO: 7 in a second PCR of the overlap PCR, and for
      introducing a TGC mutation thereto

<400> SEQUENCE: 15
acgggatcca tggcggcggc gaccggctac gactgcgttg acgacctgct gc            52

<210> SEQ ID NO 16
<211> LENGTH: 31
<212> TYPE: DNA
<213> ORGANISM: Artificial Sequence
<220> FEATURE:
<223> OTHER INFORMATION: Reverse primer for amplifynig entire sequence
      of SEQ ID NO: 7 in the second PCR of the overlap PCR

<400> SEQUENCE: 16
acccaagctt cgcgctaaac acgaagatgt c                                   31

<210> SEQ ID NO 17
<211> LENGTH: 71
<212> TYPE: DNA
<213> ORGANISM: Artificial Sequence
<220> FEATURE:
<223> OTHER INFORMATION: Forward primer for amplifying a first fragment
      of SEQ ID NO: 8 in a first PCR of an overlap PCR, and for
      introducing a TGC mutation thereto, wherein the template is SEQ ID
      NO: 5

<400> SEQUENCE: 17
acgggatccg cggcggcgac cggctacgac gcggttgacg actgcctgca ctatcacgaa    60
cgcggcaatg g                                                         71
```

```
<210> SEQ ID NO 18
<211> LENGTH: 42
<212> TYPE: DNA
<213> ORGANISM: Artificial Sequence
<220> FEATURE:
<223> OTHER INFORMATION: Reverse primer for amplifying the first
      fragment of SEQ ID NO: 8 in the first PCR of the overlap PCR, and
      for introducing a ACA mutation thereto, wherein the template is
      SEQ ID NO: 5

<400> SEQUENCE: 18
acccaagctt gttcaggtta atacattggt tcgcggtata ac                42

<210> SEQ ID NO 19
<211> LENGTH: 41
<212> TYPE: DNA
<213> ORGANISM: Artificial Sequence
<220> FEATURE:
<223> OTHER INFORMATION: Forward primer for amplifying a second fragment
      of SEQ ID NO: 8 the first PCR of the overlap PCR, and for
      introducing a TGT mutation thereto, wherein the template is SEQ ID
      NO: 5

<400> SEQUENCE: 19
gttataccgc gaaccaatgt attaacctga acgagaagag c                 41

<210> SEQ ID NO 20
<211> LENGTH: 31
<212> TYPE: DNA
<213> ORGANISM: Artificial Sequence
<220> FEATURE:
<223> OTHER INFORMATION: Reverse primer for amplifying the second
      fragment of SEQ ID NO: 8 in the first PCR of the overlap PCR, and
      for introducing a TGT mutation thereto, wherein the template is
      SEQ ID NO: 5

<400> SEQUENCE: 20
acccaagctt cgcgctaaac acgaagatgt c                            31

<210> SEQ ID NO 21
<211> LENGTH: 71
<212> TYPE: DNA
<213> ORGANISM: Artificial Sequence
<220> FEATURE:
<223> OTHER INFORMATION: Forward primer for amplifynig entire sequence
      of SEQ ID NO: 8 in a second PCR of the overlap PCR, and for
      introducing a TGC mutation thereto

<400> SEQUENCE: 21
acgggatccg cggcggcgac cggctacgac gcggttgacg actgcctgca ctatcacgaa    60
cgcggcaatg g                                                         71

<210> SEQ ID NO 22
<211> LENGTH: 31
<212> TYPE: DNA
<213> ORGANISM: Artificial Sequence
<220> FEATURE:
<223> OTHER INFORMATION: Reverese primer for amplifynig entire sequence
      of SEQ ID NO: 8 in the second PCR of the overlap PCR

<400> SEQUENCE: 22
acccaagctt cgcgctaaac acgaagatgt c                            31
```

What is claimed is:

1. A protein comprising a Serralysin protease having at least 95% identity with SEQ ID NO: 2, wherein said protease has a first cysteine residue at position 8 and a second cysteine residue at position 339.

* * * * *